(12) United States Patent
Aravamudan et al.

(10) Patent No.: US 11,804,282 B1
(45) Date of Patent: Oct. 31, 2023

(54) SYSTEMS AND METHODS FOR DRUG CLUSTERING

(71) Applicant: nference, Inc., Stoughton, MA (US)

(72) Inventors: Murali Aravamudan, Andover, MA (US); Venkataramanan Soundararajan, Andover, MA (US); Ashwin Murali, Andover, MA (US); Jeyendran Balakrishnan, Los Gatos, CA (US); Tyler Wagner, Boston, MA (US); Enrique Garcia-Rivera, Everett, MA (US)

(73) Assignee: nference, Inc., Cambridge, MA (US)

( * ) Notice: Subject to any disclaimer, the term of this patent is extended or adjusted under 35 U.S.C. 154(b) by 912 days.

(21) Appl. No.: 16/428,470

(22) Filed: May 31, 2019

Related U.S. Application Data

(60) Provisional application No. 62/678,743, filed on May 31, 2018.

(51) Int. Cl.
*G01N 33/48* (2006.01)
*G16B 15/30* (2019.01)
*G16B 40/00* (2019.01)

(52) U.S. Cl.
CPC ............... *G16B 15/30* (2019.02); *G16B 40/00* (2019.02)

(58) Field of Classification Search
None
See application file for complete search history.

(56) References Cited

U.S. PATENT DOCUMENTS

| 2017/0177834 A1* | 6/2017 | Ho et al. ............... G16C 20/30 |
| 2017/0193157 A1* | 7/2017 | Quirk et al. ........... G16B 20/20 |

OTHER PUBLICATIONS

Li, Limin. "MPGraph: multi-view penalised graph clustering for predicting drug-target interactions." IET systems biology 8.2 (2014): 67-73.*

* cited by examiner

*Primary Examiner* — Anna Skibinsky
(74) *Attorney, Agent, or Firm* — Foley Hoag LLP; David P. Halstead, J.D., Ph.D.; Lee Chedister

(57) ABSTRACT

Grouping vectors describing functional interactions between compounds and reagents into clusters identifies groups of similar compounds, and may identify drug targets, pathways of action, deleterious toxicities, immune stimulation and evasion potential, or other information regarding interactions between compounds and reagents.

41 Claims, 27 Drawing Sheets

| Cell Line | Cancer histology | Dimension score | ABL1 status | ASXL1 status |
|---|---|---|---|---|
| LAMA-84 | haematopoietic neoplasm | 0.54 | BCR-ABL+ | ASXL1 p.G646fs*12 |
| EM-2 | haematopoietic neoplasm | 0.43 | BCR-ABL+ | ASXL1 p.R693* |
| MEG-01 | haematopoietic neoplasm | 0.35 | BCR-ABL+ | ASXL1 p.G646fs*12 |
| BV-173 | haematopoietic neoplasm | 0.32 | BCR-ABL+ | |
| K-562 | haematopoietic neoplasm | 0.28 | BCR-ABL+ | ASXL1 p.Y591* |
| BE-13 | lymphoid neoplasm | 0.13 | NUP214-ABL+ | |
| EoL-1-cell | haematopoietic neoplasm | 0.12 | Rhe-PDGFRα+ | |
| HEL | haematopoietic neoplasm | <0.05 | WT | WT |
| SCC3 | lymphoid neoplasm | <0.05 | WT | WT |
| DB | lymphoid neoplasm | <0.05 | WT | WT |

Fig. 19

| Gene | Expression | p-value | Gene | Expression | p-value | Gene | Expression | p-value |
|---|---|---|---|---|---|---|---|---|
| LYL1 | Over | 2.30E-10 | MAPK14 | Over | 0.000154 | NTRK1 | Over | 0.001551 |
| USP15 | Over | 3.47E-07 | C1orf63 | Over | 0.000184 | ARHGAP26 | Under | 0.00169 |
| PBX2 | Over | 3.78E-07 | P2RY14 | Over | 0.000184 | CSF1R | Over | 0.00169 |
| MPP1 | Over | 4.50E-07 | SOCS2 | Over | 0.000184 | ABL1 | Over | 0.001712 |
| GFI1B | Over | 1.73E-06 | CFP | Over | 0.000306 | FNIP1 | Over | 0.001712 |
| HHEX | Over | 2.89E-06 | STAT5A | Over | 0.000306 | PICALM | Over | 0.001725 |
| KCNK5 | Over | 3.06E-06 | PLAGL1 | Over | 0.000415 | EIF4EBP1 | Over | 0.001883 |
| PIM1 | Over | 5.13E-06 | MTHFR | Over | 0.000626 | RUVBL2 | Over | 0.001883 |
| FAM117A | Over | 8.05E-06 | EIF3E | Over | 0.000639 | WRN | Over | 0.001883 |
| LDB1 | Over | 8.05E-06 | USP32 | Over | 0.000639 | EXT1 | Under | 0.001989 |
| RAB8A | Over | 3.10E-05 | ABCB10 | Over | 0.000804 | MLLT10 | Over | 0.002066 |
| ERG | Over | 3.21E-05 | CDT1 | Over | 0.000804 | DNAJC6 | Over | 0.002262 |
| CAMK2D | Under | 4.46E-05 | CRK | Under | 0.001015 | ALG14 | Under | 0.00232 |
| GAB2 | Over | 4.46E-05 | EEF1A1 | Over | 0.001015 | FRAT1 | Over | 0.00232 |
| STARD8 | Over | 4.46E-05 | SNX5 | Over | 0.001015 | RAB1A | Under | 0.00232 |
| STAT5B | Over | 6.06E-05 | BZRAP1 | Over | 0.001181 | SERPINB1 | Over | 0.00232 |
| TAL1 | Over | 6.06E-05 | ICAM5 | Over | 0.001263 | MTA3 | Under | 0.002683 |
| MATK | Over | 9.27E-05 | MAP3K7 | Over | 0.001263 | EPS15 | Over | 0.003079 |
| CARD8 | Over | 0.000106 | CSF3R | Over | 0.001421 | ESR2 | Over | 0.003079 |
| GATA1 | Over | 0.000137 | LMO2 | Over | 0.001421 | INHA | Over | 0.003079 |

Fig. 20

| Cell Line | Cancer histology | Dimension score | ALK gene status (mutation/amplification) | ALK gene expression level (z-score) | c-MET gene status (mut/amp/expn) |
|---|---|---|---|---|---|
| NB1 | neuroblastoma | 0.49 | Copy number = 14 (Gain/Amplification) | 4.49 (over expression) | |
| SR | lymphoid neoplasm | 0.41 | TFG/ALK+, EML4/ALK+, DDX6/ALK+, GALNT14/ALK+, ALK/SCEL+, ALK/SMEK2+, ALK/STRN+, GTF2IRD1/ALK+, TPM1/ALK+, TPM3/ALK+ | 3.31 (over expression) | |
| SF539 | glioma | 0.33 | | | |
| SCC-3 | lymphoid neoplasm | 0.27 | ALK/SCEL+, ALK/SMEK2+, ALK/STRN+ | 2.94 (over expression) | |
| DEL | small cell carcinoma | 0.27 | | 3.04 (over expression) | |
| NCI-SNU-5 | stomach adenocarcinoma | 0.25 | | | Copy number = 14 (Gain/Amplification) 3.35 (over expression) |
| KARPAS-299 | lymphoid neoplasm | 0.17 | | 3.83 (over expression) | |
| SU-DHL-1 | lymphoid neoplasm | 0.15 | NPM/ALK+, EML4/ALK+, DDX6/ALK+, ALK/SCEL+, ALK/SMEK2+, ALK/STRN+, GTF2IRD1/ALK+, TPM1/ALK+, TPM3/ALK+ | 3.52 (over expression) | |
| 639v | urinary tract carcinoma | <0.05 | WT | -2.78 | |
| HCE-4 | oesophagus carcinoma | <0.05 | WT | -3.12 | |
| NCI-H1299 | non small cell carcinoma | <0.05 | WT | -3.63 | |

Fig. 21

| Gene | Expression | p-value | Gene | Expression | p-value |
|---|---|---|---|---|---|
| SWAP70 | Under | 2.76E-09 | BCL7A | Under | 0.000333 |
| ALK | Over | 2.31E-08 | ACAP1 | Over | 0.00039 |
| IL2RA | Over | 8.68E-07 | FOXO3 | Under | 0.00039 |
| IL4R | Over | 2.00E-06 | HCK | Over | 0.000453 |
| ROR2 | Over | 2.33E-06 | CD274 | Over | 0.00077 |
| SERPINA1 | Over | 5.98E-06 | IL22 | Over | 0.000867 |
| IL2RB | Over | 1.43E-05 | ERC2 | Over | 0.001204 |
| IL7 | Over | 1.43E-05 | JUNB | Over | 0.001204 |
| USP32 | Over | 2.36E-05 | PDE4D | Over | 0.001204 |
| TNFRSF8 | Over | 2.83E-05 | PRRX2 | Over | 0.001265 |
| THPO | Over | 3.83E-05 | PRCC | Over | 0.001769 |
| HDAC4 | Over | 5.06E-05 | RUNX2 | Over | 0.001769 |
| GAS1 | Over | 8.37E-05 | STAT5B | Over | 0.001933 |
| PDGFA | Over | 9.70E-05 | SOCS1 | Over | 0.002106 |
| HUS1 | Over | 0.000111 | CTSL1 | Over | 0.002288 |
| JAK3 | Over | 0.000145 | RNF157 | Over | 0.002682 |
| CSF1R | Over | 0.000281 | RPA2 | Over | |
| PDE4DIP | Over | 0.000281 | | | |

Fig. 22

SYSTEMS AND METHODS FOR DRUG CLUSTERING

CROSS-REFERENCE TO RELATED APPLICATIONS

This application claims the benefit of U.S. Provisional Application No. 62/678,743, filed May 31, 2018, which is hereby incorporated by reference in its entirety.

BACKGROUND

Important decisions, such as which sets of compounds are likely to be associated with the same clinical phenotype and hence which specific set of compounds to promote into preclinical studies (hit-to-lead identification), are made based on parameters such as the inhibitory concentration at 50% ($IC_{50}$, the concentration of the compound at which 50% reduction in growth and division of cancer cell lines is observed) with respect to a set of target proteins, to a set of cell lines, or to other suitable parameters. The total cost of drug discovery and preclinical development exceeds $600 million per compound for complex diseases such as oncology, neurological conditions, immunological conditions, inflammatory conditions, and other diseases. Hence, there is a clear need to develop novel computational methods that can accurately predict the phenotypic relatedness of drug candidates.

Even for compounds showing stellar discovery and preclinical stage measures, there are numerous examples of failure in early- or even late-stage clinical trials (i.e., Phase II and Phase III trials). This colossal failure rate necessitates a careful and controlled clinical trial for every drug candidate before the larger regulatory approval for the compound for widespread use in human subjects. One critical determinant of regulatory approval is the satisfactory observation of efficacy and tolerance profiles for the drug candidate within a statistically significant majority of patients enrolled in clinical trials. One important function of drug candidate efficacy and safety that is used widely within both preclinical and clinical settings is a "biomarker" molecule concentration (y-axis) versus time (x-axis). These functions are used to assess the efficacy and tolerance limits of the drug candidate in each model organism as well as the human population subjected to clinical trials. Similar to the drug discovery and preclinical scenarios, the biomarker concentration (x-axis) over time (y-axis) is used to compute single-number measures of drug efficacy, toxicology, pharmacokinetics (PK), and pharmacodynamics (PD). Exactly as in the discovery, research, and preclinical settings, every human patient is generally weighted equally in computing the phenotypic efficacy of the drug candidate and regimen administered. These measures, obtained via "unbiased computational methods" that treat all subjects as equally relevant, together decide the clinical fate of each drug candidate processed by pharmaceutical R&D pipelines. These measures are also used along with the genetic, genomic, or gene expression profile of each patient to perform precision "drug-patient" matchmaking within the clinical setting after regulatory approval of the drug candidate. Improved methods for analyzing this data would help select and design improved compounds for modulating biological functions and processes.

BRIEF SUMMARY

Significant advances in medicinal chemistry and biology have yielded various measures of drug efficacy, toxicity, PK, and PD, and the last decade has seen major advances in our ability to perform high-throughput screening over large number of molecular targets (e.g., on-target drug efficacy assays, on-target drug resistance assays, off-target polypharmacology assays, etc.), cell lines, animal models, and human subjects. This trove of data opens the doors for "big data analytics." Given the rampant failure rates of drug candidates discovered and developed based on the currently popular computational methods used to assess drug efficacy and safety within discovery, preclinical, and early clinical settings, there is a need to reconsider the measures for assessment of drug safety and efficacy in this age of "big data." This disclosure provides a computational method that can identify sets of similar compounds, facilitating analogies between novel compounds and well-characterized compounds.

In accordance with one or more embodiments, a computer-implemented method of identifying similarity between compounds in a plurality of compounds is provided. The method comprises transforming each vector in a plurality of vectors, each vector in the plurality of vectors being associated with a compound in the plurality of compounds. Each component of a vector in the plurality of vectors is based on a functional interaction of the associated compound with a corresponding reagent in a plurality of reagents. Each reagent in the plurality of reagents is distinct from every other reagent in the plurality of reagents. Each vector is transformed by applying a transformation function that amplifies certain functional interactions and saturates certain other functional interactions to each component of the vector. The computer identifies at least a first and a second cluster of compounds based on the plurality of transformed vectors.

In some implementations, the method further comprises identifying a subset of reagents based on vector components that are associated with the first cluster of compounds. In some such implementations, the computer also identifies at least one biomarker associated with the subset of reagents, which may include one or more of a biomarker associated with a drug target, a biomarker associated with a drug pathway of mechanism, a biomarker associated with deleterious toxicity, a biomarker associated with an immunomodulatory signal, or some other suitable biomarker. In some implementations in which the method comprises identifying a subset of reagents, the method further comprises identifying at least one functional property associated with the subset of reagents.

A biomarker, or biological marker, is a measurable indicator of some biological state or condition. Biomarkers may be measured and evaluated to examine normal biological processes, pathogenic processes, or pharmacologic responses to a therapeutic intervention. A biomarker can be a substance whose detection indicates a particular disease state, for example, the presence of an antibody may indicate an infection. More specifically, a biomarker can indicates a change in expression or state of a protein that correlates with the risk or progression of a disease, or with the susceptibility of the disease to a given treatment. One example of a commonly used biomarker in medicine is prostate-specific antigen (PSA). This marker can be measured as a proxy of prostate size with rapid changes potentially indicating cancer. An example of a biomarker used in personalized medicine is KRAS, an oncogene that encodes a GTPase involved in several signal transduction pathways.

In some implementations, the first and the second cluster of compounds are identified based on distances between vectors associated with each compound in the first cluster of compounds and distances between vectors associated with each compound in the second cluster of compounds.

In some implementations, the method further comprises normalizing each vector in the plurality of vectors and applying the k-means clustering algorithm to the plurality of normalized vectors.

In some implementations, each reagent in the plurality of reagents is a mammalian cell line. In some such implementations, each mammalian cell line is a cancer cell line.

In some implementations, each reagent in the plurality of reagents is a protein, such as a cell receptor, an enzyme, a kinase, or some other suitable protein.

In some implementations, a component of a first vector in the plurality of vectors corresponds to the half-maximal inhibitory concentration ($IC_{50}$) of a compound on a reagent in the plurality of reagents, wherein the compound is associated with the first vector. In some implementations, a component of a first vector in the plurality of vectors corresponds to the half-maximal effective concentration ($EC_{50}$) of a compound on a reagent in the plurality of reagents, wherein the compound is associated with the first vector. In some implementations, a component of the first vector corresponds to an area under the curve (AUC) of a compound on a reagent in the plurality of reagents, wherein the compound is associated with the first vector.

In some implementations, a first component of a first vector in the plurality of vectors is associated with a first functional interaction of a first compound with a reagent, and a second component of the first vector is associated with a second functional interaction of the first compound with the same reagent.

In some implementations, literature-derived scores are appended to these vectors, representing the association between each compound and cell line combination within the scientific literature. Addition of these additional scores increases the vector dimensions.

In exemplary embodiments, local and global scores are generated using a combination of natural language processing and neural networks. Local scores capture well-known associations across the scientific literature and reflect the number of co-occurrences between two concepts within a strict window, normalized for occurrence. Global scores rely on a suite of neural networks to map associations between all concepts in the literature into a high-dimensional space. By evaluating the neighborhoods around concepts, cosine distance between global vectors provides a measure that can both recapitulate what is well-known and also identify novel connections through transitive associations.

Further details on the computation of exemplary local and global scores are available in Park, et al., Recapitulation and Retrospective Prediction of Biomedical Associations Using Temporally-enabled Word Embeddings, DOI:10.1101/627513, which is hereby incorporated by reference in its entirety.

In some implementations, the literature-derived scores between each compound and cell line pair are used as a mask to scale the importance of each cell line within every compound vector.

In accordance with one or more embodiments, a system for identifying similarity between compounds in a plurality of compounds is provided. The system comprises a computer memory and a processor. The computer memory is configured to store first data representative of functional interactions between each compound in the plurality of compounds and each reagent in a plurality of reagents, wherein each reagent in the plurality of reagents is distinct from every other reagent in the plurality of reagents. The processor is configured to transform each vector in a plurality of vectors, each vector in the plurality of vectors being associated with a compound in the plurality of compounds. Each component of a vector in the plurality of vectors is based on a functional interaction of the associated compound with a corresponding reagent in a plurality of reagents. Each vector is transformed by applying a transformation function that amplifies certain functional interactions and saturates certain other functional interactions to each component of the vector. The processor is further configured to identify at least a first and a second cluster of compounds based on the plurality of transformed vectors.

In some implementations, the processor is further configured to identify a subset of reagents based on vector components that are associated with the first cluster of compounds cluster of compounds. In some such implementations, the processor is further configured to identify at least one biomarker associated with the subset of reagents, which may include one or more of a biomarker associated with a drug target, a biomarker associated with a drug pathway of mechanism, a biomarker associated with deleterious toxicity, a biomarker associated with an immunomodulatory signal, or some other suitable biomarker. In some implementations in which the processor is configured to identify a subset of reagents, the processor further identifies at least one functional property associated with the subset of reagents.

In some implementations, the first and the second cluster of compounds are identified based on distances between vectors associated with each compound in the first cluster of compounds and distances between vectors associated with each compound in the second cluster of compounds.

In some implementations, the processor is further configured to normalize each vector in the plurality of vectors and to apply the k-means clustering algorithm to the plurality of normalized vectors.

In some implementations, each reagent in the plurality of reagents is a mammalian cell line. In some such implementations, each mammalian cell line is a cancer cell line.

In some implementations, each reagent in the plurality of reagents is a protein, such as a cell receptor, an enzyme, a kinase, or some other suitable protein.

In some implementations, a component of a first vector corresponds to the half-maximal inhibitory concentration ($IC_{50}$) of a compound on a reagent in the plurality of reagents, wherein the compound is associated with the first vector. In some implementations, a component of a first vector corresponds to the half-maximal effective concentration ($EC_{50}$) of a compound on a reagent in the plurality of reagents, wherein the compound is associated with the first vector. In some implementations, a component of the first vector corresponds to an AUC of a compound on a reagent in the plurality of reagents, wherein the compound is associated with the first vector.

In some implementations, a first component of a first vector in the plurality of vectors is associated with a first functional interaction of a first compound with a reagent, and a second component of the first vector is associated with a second functional interaction of the first compound with the same reagent.

In accordance with one or more embodiments, a computer-implemented method of identifying similarity between compounds in a plurality of compounds is provided. The method comprises normalizing each vector in a plurality of vectors, each vector in the plurality of vectors being associated with a compound in the plurality of compounds. Each component of a vector in the plurality of vectors is based on a functional interaction of the associated compound with a corresponding reagent in a plurality of reagents. Each reagent in the plurality of reagents is distinct from every other reagent in the plurality of reagents. The computer identifies at least a first and a second cluster of compounds based on the plurality of normalized vectors.

In some implementations, the method further comprises identifying a subset of reagents based on vector components that are associated with the first cluster of compounds cluster of compounds. In some such implementations, the computer also identifies at least one biomarker associated with the subset of reagents, which may include one or more of a biomarker associated with a drug target, a biomarker associated with a drug pathway of mechanism, a biomarker associated with deleterious toxicity, a biomarker associated with an immunomodulatory signal, or some other suitable biomarker. In some implementations in which the method comprises identifying a subset of reagents, the method further comprises identifying at least one functional property associated with the subset of reagents.

In some implementations, the first and the second cluster of compounds are identified based on distances between vectors associated with each compound in the first cluster of compounds and distances between vectors associated with each compound in the second cluster of compounds.

In some implementations, the method further comprises applying the k-means clustering algorithm to the plurality of normalized vectors.

In some implementations, each reagent in the plurality of reagents is a mammalian cell line. In some such implementations, each mammalian cell line is a cancer cell line.

In some implementations, each reagent in the plurality of reagents is a protein, such as a cell receptor, an enzyme, a kinase, or some other suitable protein.

In some implementations, a component of a first vector in the plurality of vectors corresponds to the half-maximal inhibitory concentration ($IC_{50}$) of a compound on a reagent in the plurality of reagents, wherein the compound is associated with the first vector. In some implementations, a component of a first vector in the plurality of vectors corresponds to the half-maximal effective concentration ($EC_{50}$) of a compound on a reagent in the plurality of reagents, wherein the compound is associated with the first vector. In some implementations, a component of the first vector corresponds to an AUC of a compound on a reagent in the plurality of reagents, wherein the compound is associated with the first vector.

In some implementations, a first component of a first vector in the plurality of vectors is associated with a first functional interaction of a first compound with a reagent, and a second component of the first vector is associated with a second functional interaction of the first compound with the same reagent.

The methods and systems disclosed herein may also be used to assess an emergent phenotype from screening compounds against other types of mammalian or non-mammalian target molecules and cell lines. For instance, in nutraceutical applications, our method can be used to identify the types of mammalian cell lines that are most responsive to particular agents, extracts, or formulations.

In some implementations, the first and second clusters may be of interest to pharmaceutical, nutraceutical, and agrochemical applications. The functional interactions may correspond to outcome measurements from one or more experiments, such as compound efficacy (e.g., sensitivity, resistance, agonistic response), toxicology (e.g., cardiac toxicity, hepatocellular toxicity), pharmacokinetics (e.g., ADME properties such as absorption, distribution, metabolism, elimination), or pharmacodynamics (e.g., PD properties such as biomarker concentrations). Some important industrial applications of the resulting phenotypic inferences within the pharmaceutical industry include: (i) selection of the optimal "hits" and discovery of prospective biomarkers from high-throughput screening (HTS) experiments conducted across large numbers of purified biomolecular targets or in-vitro cell line assays; (ii) strategic hits-to-lead compound selection and optimal biomarker validation using animal model organisms for commencing first-in-human clinical trials; (iii) patient recruitment for clinical trials based on their personalized biological information content (e.g., genomics, transcriptomics, proteomics etc.) and phenotypic manifestations; and (iv) clinical precision medicine involving monotherapies or combination therapies on a patient-by-patient basis. Some important applications within the nutraceutical industry include high-throughput screening (HTS) or rational design of compounds that are modulators of important nutraceutical targets such as vitamin synthesis or metabolism pathways, muscle-growth-related pathways (e.g., whey protein supplements), infant or toddler formula metabolism and absorption pathways (e.g., breast milk supplement), substitutes (e.g., natural sugar substitutes such as zero-calorie sweeteners), and pathways involved in interactions with beauty and lifestyle products (e.g., traditional medicine derivatives, hair strength determinants, tanning agents, dietary pills for weight loss, tonics, topical ointments, implants, sanitizers, etc.). Additional applications within the nutraceutical industry involve in-vitro assay development, in-vivo animal model development, and clinical (first-in-human) clinical testing. Within the agrochemical industry, key applications include high-throughput or rational discovery and development of one or more of fertilizers, insecticides, pesticides, preservatives (e.g., sodium benzoate), additives (e.g., gluten), adulterants (e.g., metanil yellow), flavoring agents (e.g., MSG), synergistic agrobiologics (e.g., nitrogen-fixing microbes), supplements, growth hormones, and weather-resistance-enabling agents (e.g., genetically modified organism crops) for cash crops, food crops, and other types of plants and vegetation of commercial value. Exemplary assays may involve one or more types of plant cell lines or cell cultures (e.g., rice, maize, wheat) or model organisms used to assay the phenotypes resulting from any of these types of compounds.

BRIEF DESCRIPTION OF THE SEVERAL VIEWS OF THE DRAWINGS

The systems and methods described herein are set forth in the appended claims. However, for the purpose of explanation, several implementations are set forth in the following drawings:

FIG. 19 is a table showing co-occuring BCR-ABL1 fusion and ASXL1 truncation genetic trait in an exemplary imatinib cluster.

FIG. 20 is a table is a table showing Oncogenes that are transcriptionally associated significantly with an exemplary imatinib cluster.

FIG. 21 is a table showing status of ALK mutations, ALK expression level, and ALK amplification for cell lines of an exemplary crizotinib drug cluster.

FIG. 22 is a table showing oncogenes associated with an exemplary crizotinib drug cluster.

DETAILED DESCRIPTION

The systems and methods described herein relate to identifying similarity between compounds in a plurality of compounds by grouping vectors describing functional interactions between compounds and reagents into clusters.

High Throuput Screening on Purified Proteins Insufficient to Predict Compound Similarity Let us consider imatinib and nilotinib, two compounds that were discovered by targeted screening of compound libraries against the purified BCR-ABL fusion (specifically the ABL protein kinase domain). The BCR-ABL gene fusion is an important oncogene that is frequently discovered in blood cancer samples. Both imatinib and nilotinib inhibit the catalytic activity of the ABL protein kinase domain potently ($IC_{50}$ = 600 nM and 30 nM respectively).

Figure 1:
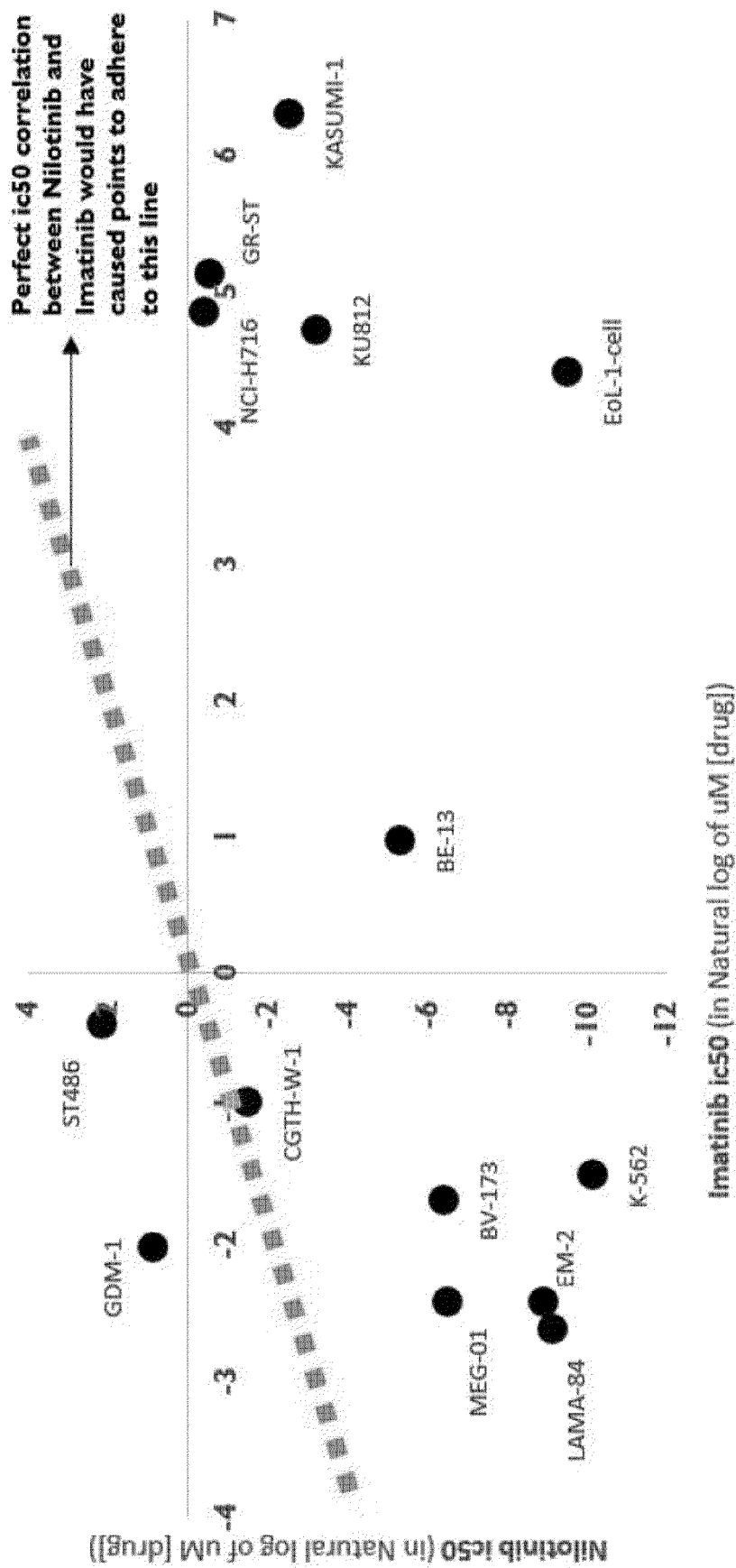
FIG. 1 is a scatter plot comparing $IC_{50}$ measurements of imatinib and nilotinib with respect to a selection of cell lines.

However, examination of phenotypic screening datasets for imatinib and nilotinib shows that their significant "on target" similarities does not extend to growth inhibition similarities. Phenotypic screening against a panel of large number of cancer cell lines was used for this analysis. Analysis of the raw $IC_{50}$ values shows significant differences in drug sensitivity and resistance profiles for imatinib and nilotinib; for instance, a majority of cell lines that are sensitive to nilotinib are resistant to imatinib, with no discernable correlation between the pairwise $IC_{50}$ values (FIG. 1). Referring to FIG. 1, a comparison of pairwise $IC_{50}$ for imatinib and nilotinib on a cell line panel is provided.

This example highlights why on-target screening of compound libraries and direct $IC_{50}$ based interpretation of such experimental data provides incomplete information to gauge relatedness of compounds. Such experiments are insufficient to identify drug candidates with likely desirable cellular phenotypes, but continue to be the first step in many drug discovery projects, often as an "in vitro screening" step preceding in vivo cell line screening. This problem is especially acute in antibody (biologics) screening, which is the standard of drug discovery for identifying promising immunotherapeutic drug candidates. This example highlights the need for in vivo cell line based phenotypic screens as the first step for drug discovery. Whole exome and whole transcriptome sequencing of all cell lines in the panel is critical for deriving hypothesis-free insights that may be subsequently experimentally validated in a highly targeted fashion.

Figure 2A:
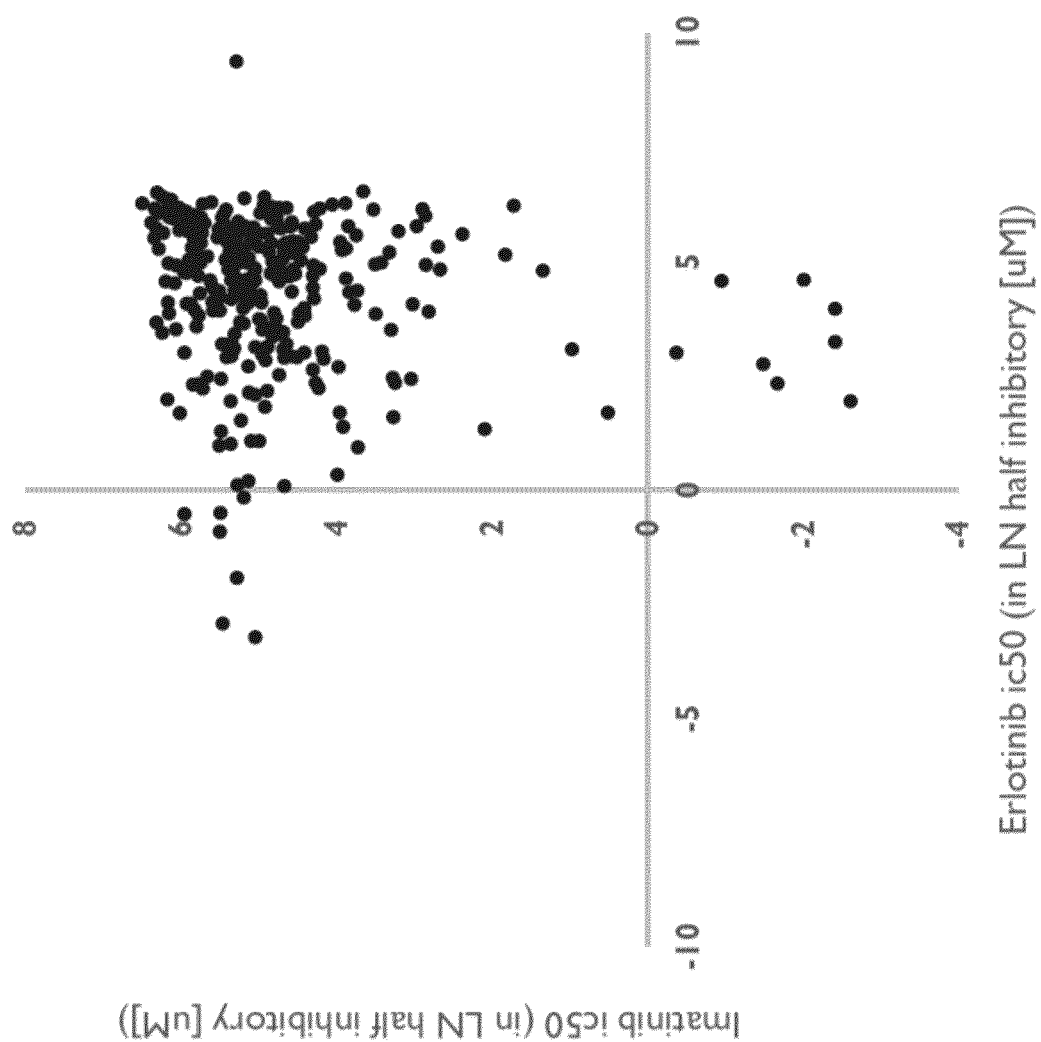
FIGS. 2A-B are a scatter plot comparing $IC_{50}$ measurements of imatinib and erlotinib and imatinib and nilotinib with respect to a selection of cell lines.
Figure 2B:
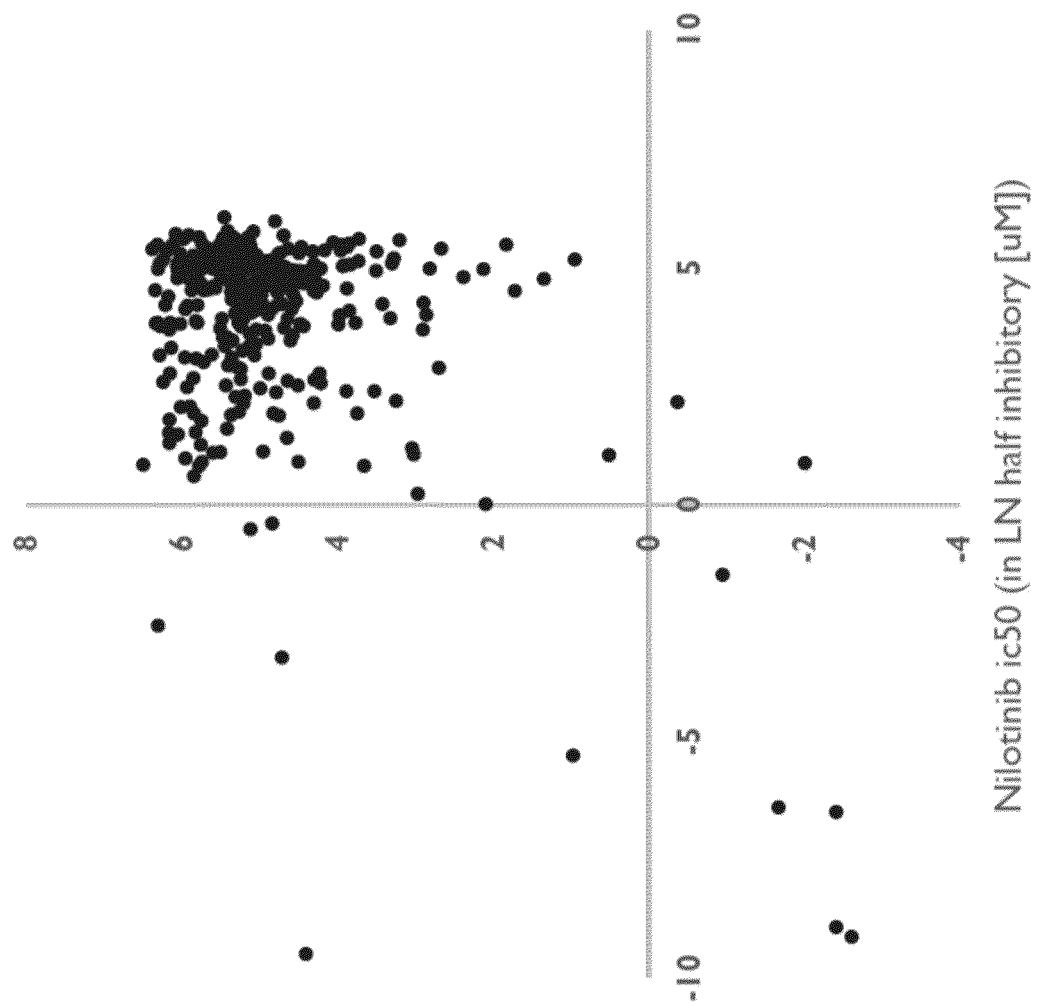

Interpretation Of Raw $IC_{50}$ Measures From Cell Line Panel Based Phenotypic Screens Measures such as $IC_{50}$ and area under the curve (AUC) are widely used for interpreting the growth inhibition rates of compounds that are phenotypically screened against cell lines. To test whether the raw $IC_{50}$ values had any useful biological insights to provide, we compared an exemplary set of FDA-approved drug pairs (imatinib-erlotinib and imatinib-nilotinib respectively). For each of these drug pairs, we plotted the raw $IC_{50}$ obtained from phenotypic screening on the same set of cell lines (FIG. 2). This analysis shows very little discriminatory utility between erlotinib and nilotinib, as both compounds appear equally similar or equally dissimilar to imatinib. Referring to FIG. 2A, a pairwise comparison of $IC_{50}$ for the imatinib-erlotinib pair of drugs on 700+ available human cancer cell lines is shown. Referring to FIG. 2B, a pairwise comparison of $IC_{50}$ for the imatinib-nilotinib pair of drugs on 700+ available human cancer cell lines is shown.

In the pre-genomic era, when there was very little genetic or transcriptional information available for each of the cell lines, little else was possible from a "biological information" standpoint, than the gross "phenotypic distinctions" of these cell lines (e.g., blood cancer cell lines versus lung cancer cell lines). However, as of May 2015, every one of these 700+ human cell lines are completely characterized from an exome (DNA) and transcriptome (RNA) standpoint, in addition to epigenetic modifications (e.g., DNA methylation), amplifications (copy number variations), proteomic information content (e.g., protein expression levels), etc. Hence, we next examined how current methods adopt "biological-hypothesis-driven" interpretation of phenotypic screening on genetically and transcriptionally well characterized cell line panels.

Figure 3:
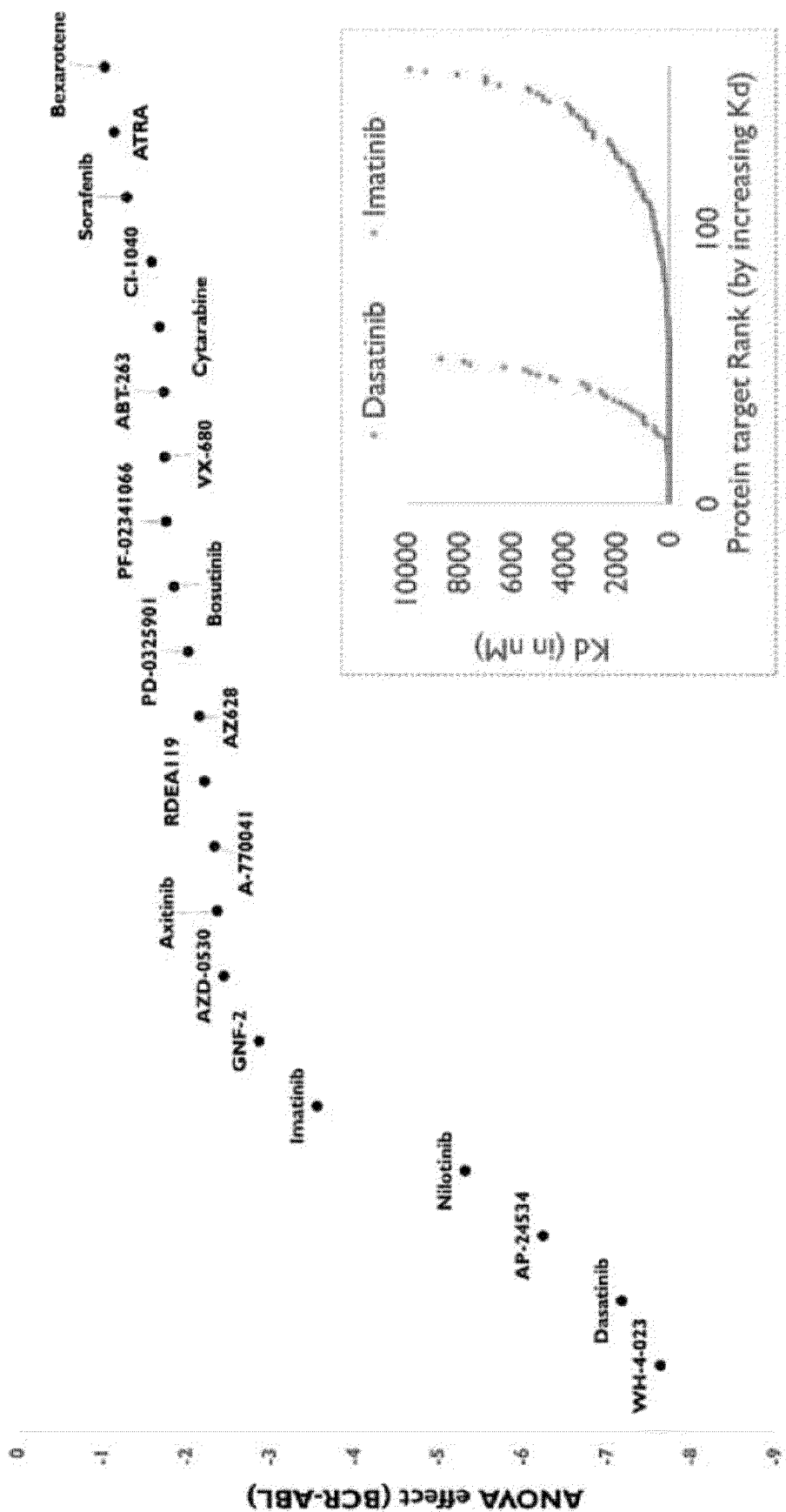
FIG. 3 is a scatter plot depicting $IC_{50}$-derived ANOVA effect values for BCR-ABL gene fusion for a set of anticancer compounds.

Hypothesis-Driven Interpretation Of Genetically Characterized Cell Line Panel Screens One important component of current drug discovery practice is generating a "dose response curve" for each compound candidate using genetically-characterized in-vitro (cell line) assays. Based on the various concentrations of each compound dosed on each cell line, and the recorded phenotypic readout, current approaches generate a "dose response curve" and compute measures of drug sensitivity such as $IC_{50}$. Gene-compound associations are then computed using methods such as ANOVA and MANOVA, based on the observed $IC_{50}$ values for each compound against the genetically-characterized cell line panel. The hypothesis is that a compound associated with a particular gene will be effective for treating conditions associated with that gene. Important decisions, such as which sets of compounds are likely to be associated with the same clinical genotype, and hence which specific set of compounds to promote into preclinical studies are made using $IC_{50}$-derived metrics like ANOVA. We examined the ANOVA effect values for BCR-ABL gene fusion (target) and VEGFR2 kinase gene (off-target) for the FDA-approved blood cancer drug imatinib, and other anti-cancer compounds. We find that compounds that are much more promiscuous than imatinib in terms of the number of molecular targets they have affinity to, such as dasatinib (see FIG. 3 inset), may nonetheless appear to be more closely BCR-ABL targeted than imatinib (FIG. 3). Thus, while the ANOVA effect provides a measure of the gene-drug association, the ANOVA effect metric of no single gene appears effective for comparing the "targetedness" of drugs.

Referring to FIG. 3, an examination of the IC50-derived ANOVA effect values for BCR-ABL gene fusion for a set of anti-cancer compounds (lower ANOVA effect value implies stronger gene-compound association) is shown, with the poly-protein screening results for dasatinib and imatinib (inset). While the ANOVA effect values suggest that dasatinib is more strongly associated with the BCR-ABL gene fusion drug target than imatinib, the proteome-wide screening data suggests that dasatinib (binds over 160 distinct purified proteins) is far less targeted than imatinib (binds less than 50 distinct purified proteins). Thus, the ANOVA effect measure for BCR-ABL gene fusion is misleading for this illustrative example of predicting "targetedness" of anti-cancer compounds.

Figure 4:
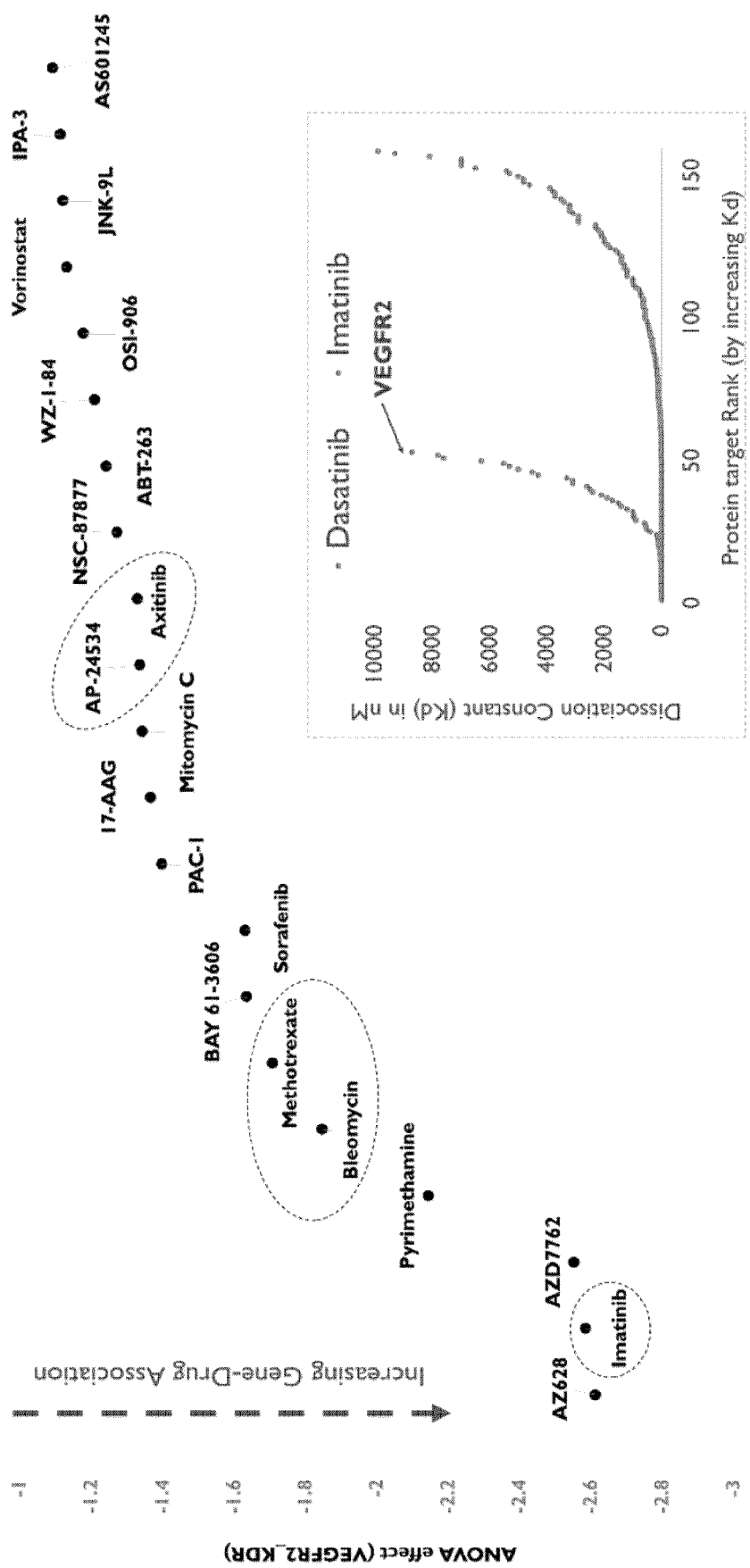
FIG. 4 is a scatter plot depicting $IC_{50}$-derived ANOVA effect values for VEGFR2 (KDR) gene for a set of anti-cancer compounds.

We next examined the ANOVA effect for the VEGFR2 (KDR) gene for imatinib and other anti-cancer compounds. While imatinib has almost no affinity to the VEGFR2 protein (FIG. 4 inset), we find that imatinib has one of the best ANOVA effect values for the VEGFR2 gene. In addition to this misleading observation, we further find that non-specific DNA-damaging chemotherapeutic agents have a higher VEGFR association than the VEGFR2-targeted drugs like axitinib, AP-24534/ponatinib, and sorafenib (FIG. 4). Finally, the VEGFR2-targeted drugs sunitinib and pazopanib do not show any VEGFR2 association at all. Taken together, the VEGFR2 ANOVA effect analysis discussed here highlights why ANOVA effect appears to be a poor metric for evaluating drug relatedness to any considered gene.

Referring to FIG. 4, examination of the IC50-derived ANOVA effect values for the VEGFR2 (KDR) gene for a set of anti-cancer compounds (lower ANOVA effect value implies stronger gene-compound association) is shown, with the poly-protein screening results for dasatinib and imatinib (inset highlighting poor affinity of imatinib for VEGFR2). The ANOVA effect values suggest imatinib is more significantly VEGFR2 associated than non-specific DNA damaging agents (methotrexate, bleomycin), which in turn are more VEGFR associated than AP-24535 (ponatinib), axitinib etc that are in reality the major VEGFR2 targeted drugs. This example shows ANOVA effect is ineffective as an aid to predict genetic relatedness of drugs and drugdrug relatedness.

Need for Hypothesis-Free Learning From Genetically-Characterized Phenotypic Screens The usual approach—computing ANOVA effect values for all known oncogenes—suffers from the shortcomings of our incomplete knowledge of specific oncogenes driving specific types of tumors. Additionally, non-oncogene genes that impinge on drug efficacy, toxicity, and resistance are missed by the ANOVA-based approaches. Moreover, hypothesis-driven (ANOVA and MANOVA) methods have only examined around 60 "known" oncogenes for drug associations. Such a restricted genetic factor discovery negatively impacts drug response predictions, and may actually contribute to unfavorable clinical outcomes. While methods like ANOVA have contributed to unearthing potential gene-drug associations, they do not provide any obvious route to assessing drug-drug similarity. The inventors have realized that a less myopic method that adopts a non-dogmatic (hypothesis-free) approach to assessing similarity of compounds and identify emergent properties is required to maximize the value of phenotypic screens. Such hypothesis-free clustering of drugs can motivate the assessment of genomic and transcriptomic traits that are uniquely shared by the cell lines that maximally contribute to each cluster.

The systems and methods disclosed herein may be applied to predict pharmaceutically-salient clinical factors such as efficacy, toxicity, and resistance from phenotypic screens on large numbers of genetically and transcriptionally well-characterized cell line panels. It may also shed light on putative mechanistic basis for drug action leading to efficacy of therapeutic regimens, off-target associations that potentially cause deleterious toxicity in specific organs, and possible immuno-modulatory signals that warrant further targeted experimental validation studies.

Constructing a Vector Space

Each compound's response in a set of cell lines is characterized as a vector in a Drug Space, which has a basis corresponding to the set of cell lines and in which the component of the drug vector along a basis vector is based on the compound's response in a specific cell line.

We elect to characterize each cell line as a vector based on its underlying genetic code, expressed as features. Specifically, the set of all somatic mutations, copy number alterations, and RNA expression levels define the dimensions (comparable to an alphabet) by which a cell line is characterized. Since the number of genetic features (such as somatic mutations) easily ranges in millions, each cell line constitutes a vector in a high-dimensional cell feature space (or Mutation Space).

More formally, let $m_i$ represent the $i^{th}$ genetic feature (or mutation) in the cell feature space (or Mutation Space) $\{m_1 \ldots m_M\}$ where M is the total number of features (e.g., somatic mutations). As a concrete example, {EGFR_p.L858R, KRAS_pG12D, BCR/ABL1, ....} form a cell feature space (or Mutation Space) with well-known point mutations and gene fusions that occur in various types of cancers. Each cell line typically has a much smaller set of genetic features (e.g., mutations) compared to the set of all features (or mutations). We represent each cell line as an M-dimensional binary vector where the $i^{th}$ element of the vector is 1 if mutation $m_i$ is present in the given cell line and 0 otherwise.

The ideal basis set for a Drug Space of size N will be made up of N cell lines, where the inner product of any pair of cell lines in the cell feature space (or Mutation Space) will be 0 (corresponding to a complete set of N orthogonal basis). In practice, any linearly independent basis (i.e., the inner products of any pair of cell lines is not 1) will do; preferably, the inner product of any pair of cell lines will be close to 0 to allow for easier interpretation of relationships between different drug vectors.

We will illustrate the vector space in 2 dimensions before generalizing to N dimensions. Let there be two cell lines $cl_1$ and $cl_2$ which share no mutations (i.e., the inner product of the two binary vectors in the cell feature space (or Mutation Space) is 0). Let drug $dr_1$ be very potent to cell line $cl_1$ (i.e., $dr_1$ very effectively inhibits growth of cell line $cl_1$ and hence has an $IC_{50}$ value less than $-T$ in log micromolar scale). Let drug $dr_1$ also be completely ineffective against cell line $cl_2$ (the $IC_{50}$ value is a high positive number in log micromolar scale). $dr_1$ is represented by $[e^{kT}, 0]$. Let drug $dr_2$ have the exact opposite characteristics: it is highly potent against $cl_2$ but completely ineffective against $cl_1$. The drug vector corresponding to $dr_2$ is $[0, e^{kT}]$. Let drug $dr_3$ be equally effective against $cl_2$ and $cl_1$. The drug vector corresponding to $dr_3$ is $[e^{kT}, e^{kT}]$. Then, whenever the angle of a drug vector with respect to a specific dimension approaches 0°, the corresponding drug is most potent to the cell line that dimension represents; when a drug vector has equal angles to all the dimensions, the corresponding drug is equally potent to all cell lines. Thus $dr_3$ subtends a 45° angle with respect to both cell lines $cl_2$ and $cl_1$. A drug with a vector lying between $dr_2$ and $dr_3$ is more potent to cell line $cl_2$ and less potent to cell line $cl_1$; similarly, a drug with a vector lying between $dr_1$ and $dr_3$ is more potent to cell line $cl_1$ and less potent to cell line $cl_2$.

This notion may be extended to an N-dimensional space, in which we represent each drug's reaction to the chosen N cell lines as a vector. The components of such a vector correspond to transformed $IC_{50}$ measures of the drug against the cell line that corresponds to a certain dimension, where the $IC_{50}$ measures are transformed according to a mechanistic transformation function (MTF) as described above. Each drug vector is represented below by Equation (1), where the $i^{th}$ component of the N-dimensional drug vector is associated with an $IC_{50}$ measure corresponding to the $i^{th}$ cell line:

$$\vec{d_k} = \begin{bmatrix} c_1 \\ c_2 \\ \cdot \\ \cdot \\ c_{N-1} \\ c_N \end{bmatrix}, c_i = f\left(IC_{50} \text{ of } i^{th} \text{ cell line}\right) \quad (1)$$

The inner product between any two n-dimensional vectors $[a_1, a_2, \ldots, a_n]$ and $[b_1, b_2, \ldots, b_n]$ is related to the cosine of the angle $(\cos\theta)$ between the vectors, as described in Equation 2:

$$\cos\theta = \frac{\sum_{i=1}^{N} a_i b_i}{\|a_i\| \|b_i\|} \text{ where } \|a_i\| = \sqrt{\sum_{i=1}^{N} a_i^2} \text{ and } \|b_i\| = \sqrt{\sum_{i=1}^{N} b_i^2} \quad (2)$$

The inner product of a pair of drug vectors $\vec{d_j}$ and $\vec{d_k}$ is thus related to the cosine of the angle between them in the N-dimensional space. If the angle between the two drug vectors is less than a certain threshold, we can say that the vectors—and their corresponding compounds—are similar in eliciting similar responses on a set of cell lines.

While the foregoing discussion has used $IC_{50}$ as an illustrative example, the same concept may be applied to other functional interactions. As used herein, a "functional interaction" between a compound and a reagent refers to any observable, detectable, or otherwise ascertainable characteristic resulting from, or associated with, the interaction of the compound with the reagent. For example, a functional interaction between a compound and a reagent can be the affinity of the compound for the reagent (or vice versa), e.g., where the reagent is a protein, such as a kinase or other enzyme. Similarly, where the reagent has a measurable activity (e.g., against a kinase or other cellular enzyme), the functional interaction can be modulation of the reagent's activity by the compound. In another example, where the reagent is a proliferating cell (e.g., a cancer cell), the functional interaction can be the inhibition of the growth, viability, or motility of the cell by the compound. In yet another example, where the reagent is a Caco-2 cell/cell monolayer (or other cell utilized to measure intestinal permeability of compounds), the functional interaction can be traversal of the compound across the monolayer. In another example, where the reagent is an animal (e.g., a rodent or other non-human animal model of disease), the functional interaction can be the toxicity of the compound. And in yet another example, a functional interaction can be the metabolism of the compound by the reagent (e.g., where the reagent is a cell, enzyme (e.g., Cytochrome P450), or an animal).

One of skill in the art will appreciate the myriad ways that functional interactions can be measured and/or represented. In one non-limiting example, binding interactions can be represented by, e.g., affinity constant ($K_D$), dissociation constant ($k_d$), or association constant ($k_a$). In another example, intestinal permeability can be represented as an efflux ratio. In another example, the toxicity of a compound in a non-human animal can be represented as a median lethal dose ($LD_{50}$). Inhibition of the activity of a reagent can be represented or measured by the half-maximal inhibitory concentration ($IC_{50}$), and inhibition of cell growth can be measured or represented as half-maximal effective concentration (or $EC_{50}$). Another suitable metric for cell growth/inhibition is the area under the dose response curve for a given cell line dosed with varying concentrations of a compound. The pharmacokinetic properties of a compound in an animal can also be measured or represented as a half-life ($T_{1/2}$).

Figure 5:
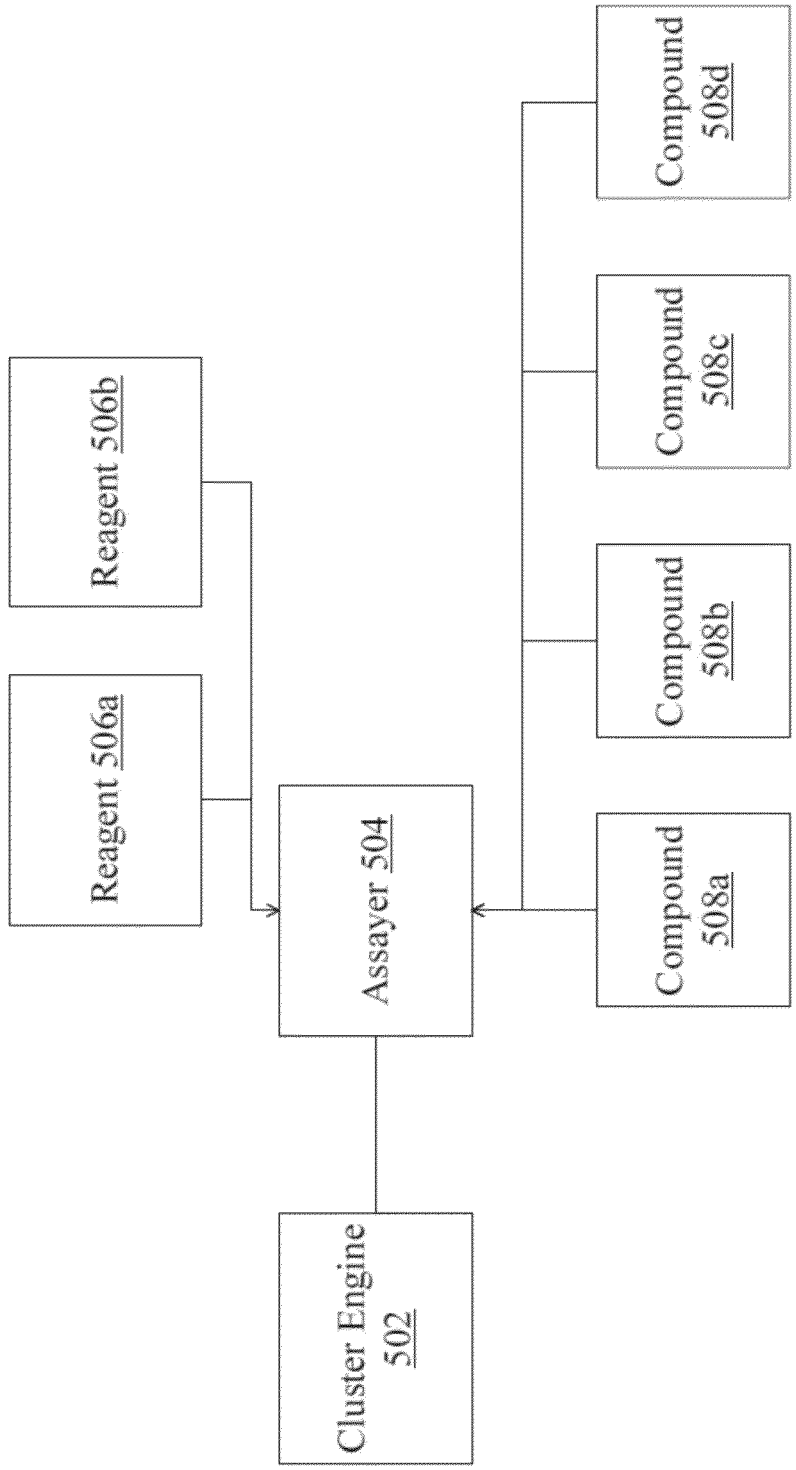
FIG. 5 is a block diagram for a system for identifying similarity between compounds in a plurality of compounds, according to an illustrative implementation.

FIG. 5 is an illustrative block diagram of a cluster system 500. As depicted, cluster system 500 comprises a cluster engine 502 and an assayer 504. Cluster engine 502 is described in more detail with respect to FIG. 6. Assayer 504 gathers data regarding functional interactions between reagents 506a and 506b (collectively, reagents 506) and compounds 508a-508d (collectively, compounds 508). Reagents 506 may include mammalian cell lines, cancer cell lines, proteins, cell receptors, enzymes, kinases, or any other suitable targets, and there may be a different number of reagents 506 than are here depicted. Compounds 508 may include molecules, antibodies, or any other suitable compounds, and there may be a different number of compounds 508 than are here depicted. Assayer 504 may gather one or more varieties of data regarding functional interactions between a reagent 506 and a compound 508, such as a reduction in activity, an increase in activity, or other suitable functional interactions. Cluster engine 502, or in some implementations assayer 504, may transform such data into overall measurements of functional interactions, such as an $IC_{50}$, a half-maximal effective concentration ($EC_{50}$), or other suitable measurements. As depicted, cluster engine 502 is directly connected to assayer 504, but in some implementations cluster engine 502 may receive data from one or more assayers 504 via a computer network, a removable data storage device such as a USB memory stick, or through some other suitable means. As an illustrative example, data produced by assayer 504 may be stored on a separate computer for a period of time before being transmitted to cluster engine 502.

Figure 6:
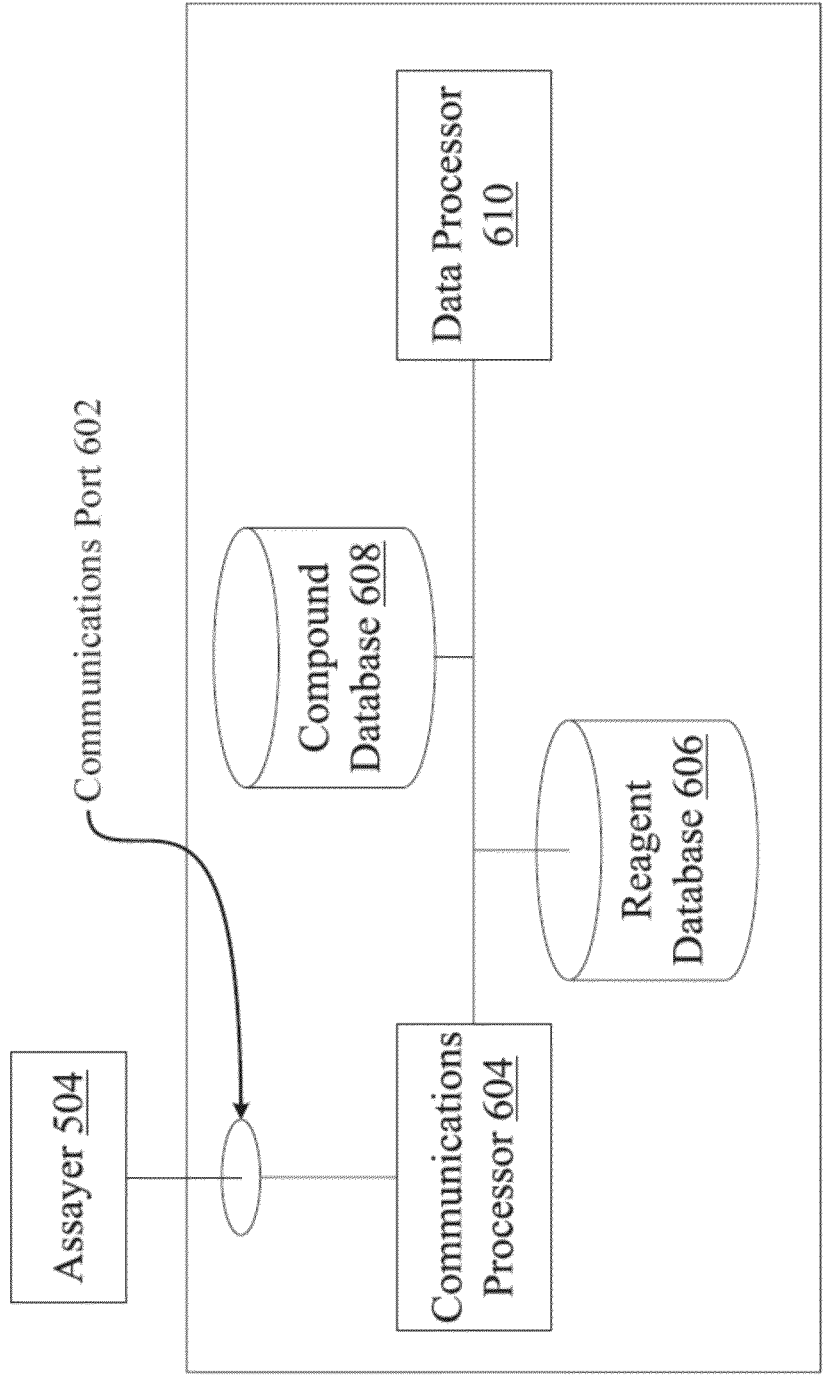
FIG. 6 is a block diagram of an engine for identifying similarity between compounds in a plurality of compounds, according to an illustrative implementation.

FIG. 6 is a block diagram of a cluster engine 600, which may be a personal laptop computer, a personal desktop computer, a server, a computer cluster, or some other suitable computing device. Cluster engine 600 identifies similarity between compounds in a plurality of compounds, and may act as the cluster engine 502 depicted in FIG. 5. Cluster engine 600 transmits and receives data through communication port 602. Communications processor 604 may request and receive data representative of functional interactions of compounds with reagents through communication port 602. Reagent database 606 may store information about reagents, which may include information regarding identifying and interpreting raw data received from assayer 504, one or more transformation functions associated with a functional reaction of a reagent and a compound, one or more biomarkers associated with the reagent, or other suitable information. Compound database 608 may store information regarding compounds, including measurements of functional interactions between a compound and reagents, user-provided information regarding a compound (e.g., a set of cancers that a compound is already known to target), or other suitable information. Data processor 610 may transform raw data into one or more measurements of functional interactions between a compound and a reagent, transform such measurements, divide compounds into two or more clusters based on transformed measurements, or perform other suitable actions.

The depicted communications port 602 is a data port which transmits requests for and receives data from assayer 504. The data requested and received may include raw data regarding functional interactions between a compound and a reagent (e.g., dose-response data), a measurement of functional interactions between a compound and a reagent (e.g., an $IC_{50}$ or an $EC_{50}$), or other suitable data. In some implementations, communications port 602 may be directly connected to an assayer 504 or to a memory storage device containing information generated by assayer 504. In such implementations, communications port may include an RS232 port, a serial port, a USB port, or some other suitable port. In some implementations, communications port 602 may be connected to one or more assayers 504 or to a memory storage device storing data from one or more assayers 504 via a computer network such as the Internet. In such implementations, communications port 602 may include a 100BASE-TX port, a 1000BASE-T port, a 10 GBASE-T port, a WI-FI antenna, a BLUETOOTH antenna, a cellular antenna, or other suitable network ports. In certain implementations, there may be a different number of ports than are depicted. In certain implementations, communication port 602 may provide secure communications, such as by using the Secure Sockets Layer (SSL) protocol, the Transport Layer Security (TLS) protocol, or other suitable protocol.

Communications processor 604 may be a computer processor that sends and receives information via communications port 602. In response to instructions received from data processor 610, communications processor 604 may request data from an assayer 504 or transmit other suitable data. Communications processor 604 may further forward or act on data received through communications port 602, such as recording data received from an assayer 504 in compound database 608, forwarding such data to data processor 610, or taking some other suitable measure.

Reagent database 606 may be a computer-readable and -writable medium storing information about one or more reagents, which may include information regarding how to identify data from an assayer 504 as being associated with a reagent, computer instructions on how to derive measurements of functional interactions from raw data, one or more transformation functions associated with one or more measurements of functional interactions with the reagent, one or more biomarkers associated with the reagent, or other suitable information.

Compound database 608 may be a computer-readable and -writable medium storing information regarding compounds, which may include raw data regarding functional interactions between a compound and one or more reagents, measurements—transformed, untransformed, or both—of functional interactions between a compound and one or more reagents, user-provided information regarding a compound (e.g., a set of cancers that the compound is known to target), or other suitable information. In some implementations, compound database 208 may be combined with reagent database 606.

Data processor 610 may be a computer processor that identifies similarity between compounds in a plurality of compounds based on the data received from an assayer 504 and stored in reagent database 606 and compound database 608. As described in relation to FIG. 7, data processor 610 may generate a vector describing a compound in which each component corresponds to a measurement of a functional interaction between the compound and a reagent. Data processor 610 may further transform such vectors, which may include normalizing the vectors or transforming them based on one or more transformation functions, which may be stored in reagent database 606 or included in the code instructing data processor 610. Data processor 610 identifies similarity between compounds by grouping compounds into clusters based on their vectors, and may further act on such information as described in relation to FIG. 8.

Similarity engine 600 identifies similarity between compounds in a plurality of compounds. Communications processor 604 receives data regarding each compound's functional interactions with reagents from an assayer 504 via communications port 602. If the received data is in a raw form, communications processor 604 may forward such data to data processor 610 for derivation of a measurement of the functional interaction, such as an $IC_{50}$ or an $EC_{50}$. Any such measurements, and in some implementations the raw data, are stored in compound database 608. Data processor 610 generates mathematical descriptions of compounds by generating a vector in which each component corresponds to a measurement of a functional interaction between the compound and a reagent. Data processor 610 may further transform such vectors, such as by normalizing the vectors or transforming the vectors based on one or more transformation functions stored in reagent database 606.

Data processor 610 identifies clusters of vectors, and may identify similarity between compounds based on which cluster the compounds' vectors were assigned to.

Figure 7:
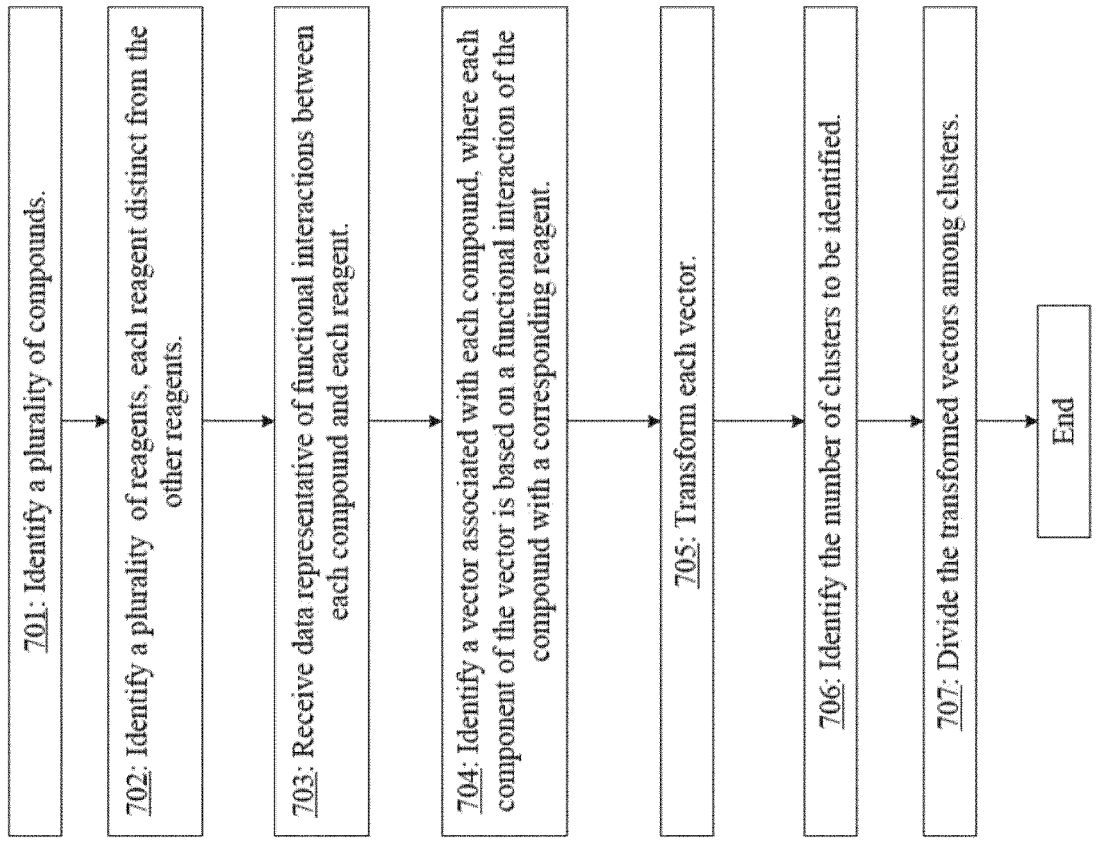
FIG. 7 is a flow chart of a process for identifying similarity between compounds in a plurality of compounds, according to an illustrative implementation.

FIG. 7 is an illustrative flow chart of a clustering process 700. Process 700 identifies similarity between compounds. Referring to FIG. 6, process 700 begins with step 701, in which data processor 610 identifies a plurality of compounds, such as by receiving user instructions identifying compounds to be compared. In step 702, data processor 610 identifies a plurality of reagents, where each reagent is distinct from the other reagents; and in step 703, data processor 610 instructs communications processor 604 to retrieve data representative of functional interactions between each identified compound and each identified reagent. In some implementations, the order of steps 701-703 may be changed: as an illustrative example, communications processor 604 may receive and record functional interaction data, and data processor 610 may then identify compounds, reagents, and functional interaction data that was received.

In step 704, data processor 610 identifies a vector associated with each compound. Each component of such a vector is based on a functional interaction of the compound associated with the vector with a reagent, and each vector identified takes the same form. As an illustrative example, if compounds were being compared based on their interactions with two different reagents, each compound might be associated with a vector of the form (a, b), where a represents the $IC_{50}$ of the compound with respect to the first reagent and b represents the $IC_{50}$ of the compound with respect to the second reagent. In some implementations, some components of vectors may represent different functional interactions between the associated compound and a single reagent.

In step 705, data processor 610 transforms each vector identified in step 704. Step 705 may include one or more of applying a function to each component of each vector, normalizing each vector, or otherwise transforming each vector. In some implementations in which a function is applied to each component of each vector, the same function is applied to every component of the vector; in some alternative implementations, a function corresponding to a functional interaction with a reagent may be applied to the component of vectors that corresponds to the same functional interaction with the same reagent, while a different function may be applied to other components of the vectors.

In step 706, cluster engine 600 identifies the number of clusters to be identified. The number of clusters to be identified may be received from a user through communications processor 604, may be identified through a formula or algorithm either received from a user through communications processor 604 or programmed into data processor 610, or through some other suitable method. As an illustrative example of identifying a number of clusters through a formula, data processor 610 may set the number of clusters to the closest integer to the square root of half of the number of compounds. As an illustrative example of identifying a number of clusters based on an algorithm, data processor 610 may apply the jump method to the vectors to identify the number of clusters. In some implementations, step 706 may occur earlier in process 700, such as by a user selecting an algorithm to identify the number of clusters at the very start of the process.

Process 700 ends with step 707, in which data processor 610 divides the transformed vectors into the number of clusters identified in step 706. Data processor 610 may assign vectors to clusters using k-means clustering algorithm, the k-medoids clustering algorithm, the filtering algorithm, or some other suitable algorithm. The algorithm used may be based on Euclidean distances between vectors, cosine similarity between vectors, or some other suitable metric.

Figure 8:
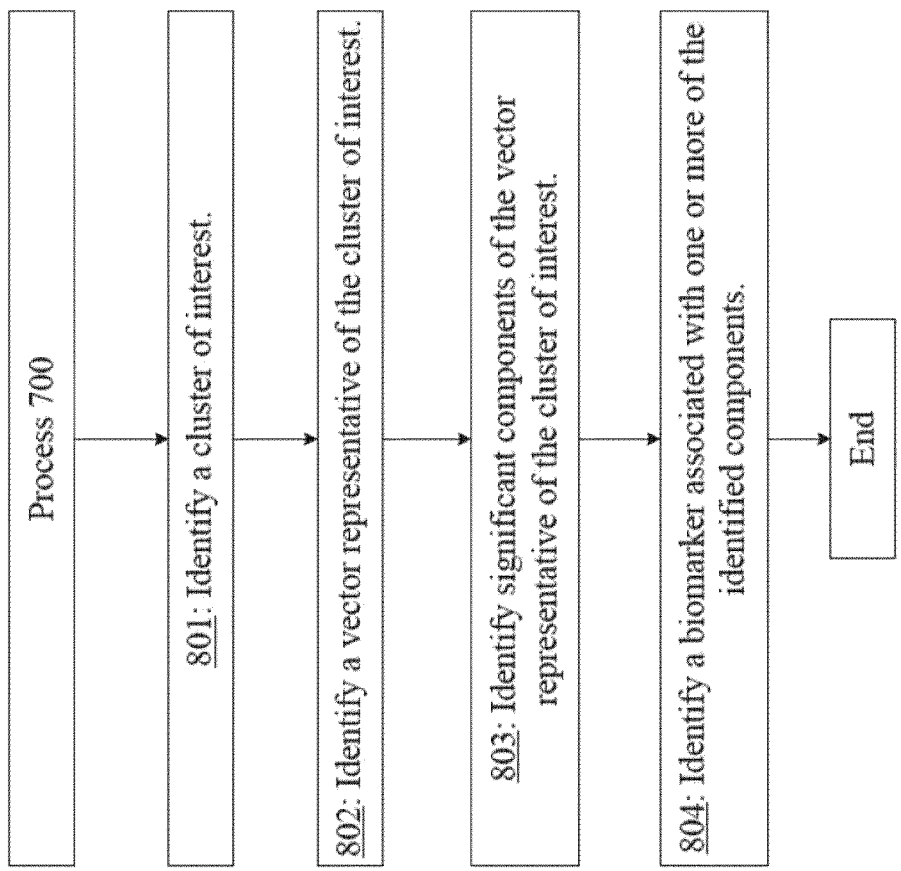
FIG. 8 is a flow chart of a process for identifying biomarkers associated with a cluster of related compounds, according to an illustrative implementation.

FIG. 8 is an illustrative flow chart of a biomarker identification process 800. Biomarker identification process 800 may be used to identify biomarkers (e.g., drug targets, drug pathways of action, deleterious toxicities, immunomodulatory signals, or other suitable biomarkers) or functional properties associated with a cluster of drugs. Referring to FIG. 7, once process 700 has been completed, process 800 may begin with step 801, in which a cluster of interest is identified, such as by communications processor 604 receiving user instructions identifying a cluster. In step 802, data processor 610 identifies a vector representative of the cluster of interest. The vector identified may be a mean of its corresponding cluster, a medoid of its corresponding cluster, a median of its corresponding cluster, or may be identified in some other suitable fashion. In some implementations, data processor 610 may identify a vector representative of each cluster identified in process 700; in some such implementations, step 802 may precede step 801.

In step 803, data processor 610 identifies significant components of the vector representing the cluster of interest. Components may be designated as significant based on whether they are greater than a predetermined threshold, greater than the median size of each component in the representative vector, in the top quintile of components by length of the representative vector, or based on some other suitable criteria. Process 800 ends with data processor 610 identifying a biomarker associated with one or more of the identified components based on information stored in reagent database 606. Illustrative examples of biomarkers that process 800 may identify include the site of a cancer (e.g., breast cancer or lung cancer), histology (e.g., adenocarcinoma or non-small cell), point mutations (e.g., single-nucleotide polymorphisms), gene fusions, gene amplifications, gene expression, protein expression, drug targets, drug pathways of action, deleterious toxicities, and immunomodulatory signals.

Figure 9:
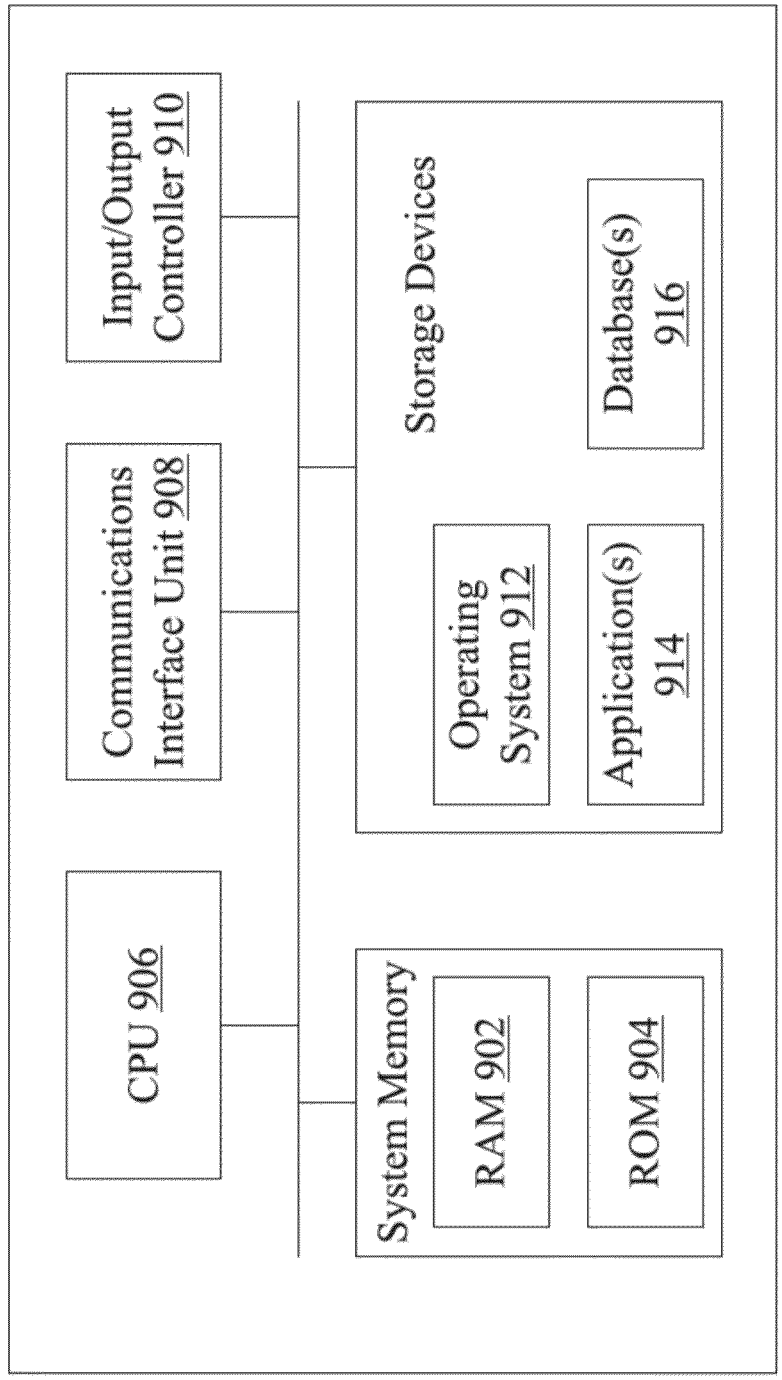
FIG. 9 is a block diagram of a computing device for performing any of the processes described herein, according to an illustrative implementation.

FIG. 9 is a block diagram of a computing device that can be used to implement or support any of the components of the systems of FIGS. 5 or 6, and for performing any of the processes described herein. Cluster engine 600 may be implemented on one or more computing devices 900 having suitable circuitry, and cluster engine 502 may communicate with assayer 504 through one or more computing devices 900 having suitable circuitry. In certain aspects, a plurality of the components of cluster system 500 may be included within one computing device 900. In certain implementations, a component of similarity system 500 may be implemented across several computing devices 900.

The computing device 900 comprises at least one communications interface unit, an input/output controller 910, system memory, and one or more data storage devices. This can support a network connection such as described in relation to communication port 602 in FIG. 6. The system memory includes at least one random access memory (RAM 902) and at least one read-only memory (ROM 904). RAM 902 can support the compound database 608 of FIG. 6, for example. All of these elements are in communication with a central processing unit (CPU 906) to facilitate the operation of the computing device 900. The computing device 900 may be configured in many different ways. For example, the computing device 900 may be a conventional standalone computer or alternatively, the functions of computing device 900 may be distributed across multiple computer systems and architectures. In FIG. 9, the computing device 900 may be linked, via network or local network, to other servers or systems.

The computing device 900 may be configured in a distributed architecture, wherein databases and processors are housed in separate units or locations. Some units perform primary processing functions and contain, at a minimum, a general controller or a processor and a system memory. In distributed architecture implementations, each of these units may be attached via the communications interface unit 908 to a communications hub or port (not shown) that serves as a primary communication link with other servers, client or user computers, and other related devices. The communications hub or port may have minimal processing capability itself, serving primarily as a communications router. A variety of communications protocols may be part of the system, including, but not limited to: Ethernet, SAP, SAS™, ATP, BLUETOOTH™, GSM, and TCP/IP The CPU 906 comprises a processor, such as one or more conventional microprocessors and one or more supplementary co-processors such as math co-processors for offloading workload from the CPU 906. The CPU 906 is in communication with the communications interface unit 908 and the input/output controller 910, through which the CPU 906 communicates with other devices such as other servers, user terminals, or devices. The communications interface unit 908 and the input/output controller 910 may include multiple communication channels for simultaneous communication with, for example, other processors, servers, or client terminals.

The CPU 906 is also in communication with the data storage device. The data storage device may comprise an appropriate combination of magnetic, optical, or semiconductor memory, and may include, for example, RAM 902, ROM 904, flash drive, an optical disc such as a compact disc, or a hard disk or drive. The CPU 906 and the data storage device each may be, for example, located entirely within a single computer or other computing device; or connected to each other by a communication medium, such as a USB port, serial port cable, a coaxial cable, an Ethernet cable, a telephone line, a radio frequency transceiver, or other similar wireless or wired medium or combination of the foregoing. For example, the CPU 906 may be connected to the data storage device via the communications interface unit 908. The CPU 906 may be configured to perform one or more particular processing functions.

The data storage device may store, for example, (i) an operating system 912 for the computing device 900; (ii) one or more applications 914 (e.g., computer program code or a computer program product) adapted to direct the CPU 906 in accordance with the systems and methods described here, and particularly in accordance with the processes described in detail with regard to the CPU 906; or (iii) database(s) 916 adapted to store information that may be utilized to store information required by the program. The depicted database 916 can be any suitable database system, and can be a local or distributed database system.

The operating system 912 and applications 914 may be stored, for example, in a compressed, an uncompiled and an encrypted format, and may include computer program code. The instructions of the program may be read into a main memory of the processor from a computer-readable medium other than the data storage device, such as from the ROM 904 or from the RAM 902, or from a computer data signal embodied in a carrier wave, such as that found within the well-known Web pages transferred among devices connected to the Internet. While execution of sequences of instructions in the program causes the CPU 906 to perform the process steps described herein, hard-wired circuitry may be used in place of, or in combination with, software instructions for implementation of the processes of the present disclosure. Thus, the systems and methods described are not limited to any specific combination of hardware and software.

Suitable computer program code may be provided for performing one or more functions in relation to functional similarity quantification system as described herein. The program also may include program elements such as an operating system 912, a database management system, and "device drivers" that allow the processor to interface with computer peripheral devices (e.g., a video display, a keyboard, a computer mouse, etc.) via the input/output controller 910.

The term "computer-readable medium" as used herein refers to any non-transitory medium that provides or participates in providing instructions to the processor of the computing device 900 (or any other processor of a device described herein) for execution. Such a medium may take many forms, including but not limited to, non-volatile media and volatile media. Non-volatile media include, for example, optical, magnetic, or opto-magnetic disks, or integrated circuit memory, such as flash memory. Volatile media include dynamic random access memory (DRAM), which typically constitutes the main memory. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM or EEPROM (electronically erasable programmable read-only memory), a FLASH-EEPROM, any other memory chip or cartridge, or any other non-transitory medium from which a computer can read.

Various forms of computer readable media may be involved in carrying one or more sequences of one or more instructions to the CPU 906 (or any other processor of a device described herein) for execution. For example, the instructions may initially be borne on a magnetic disk of a remote computer (not shown). The remote computer can load the instructions into its dynamic memory and send the instructions over an Ethernet connection, cable line, or even telephone line using a modem. A communications device local to a computing device 900 (e.g, a server) can receive the data on the respective communications line and place the data on a system bus for the processor. The system bus carries the data to main memory, from which the processor retrieves and executes the instructions. The instructions received by main memory may optionally be stored in memory either before or after execution by the processor. In addition, instructions may be received via a communication port as electrical, electromagnetic, or optical signals, which are exemplary forms of wireless communications or data streams that carry various types of information.

Some implementations of the above described may be implemented by the preparation of application-specific integrated circuits or by interconnecting an appropriate network of conventional component circuits, as will be apparent to those skilled in the art. Those of skill in the art would understand that information and signals may be represented using any of a variety of different technologies and techniques. For example, data, instructions, requests, information, signals, bits, symbols, and chips that may be referenced throughout the above description may be represented by voltages, currents, electromagnetic waves, magnetic fields or particles, optical fields or particles, or any combination thereof.

Examples

Here we primarily use the phenotypic screening and genomic characterization datasets from the Wellcome Trust Sanger Institute (Hinxton UK) and the MGH Cancer Center (Boston MA). The cell line growth inhibition datasets contain 1,000+ cancer cell lines and 139 anti-cancer drugs. The whole exome sequence is available for all of the cell lines from this study, using the Illumina GAII or HiSeq DNA sequencers. This was corroborated with the NCI-60 whole exome sequencing data as well. All genetic mutations including single nucleotide polymorphisms (SNPs) and structural rearrangements (insertions, deletions, fusions) were thus obtained for our analysis. In addition to the exome data, gene expression datasets from Affymetrix Human Genome U219 Array and DNA copy number variations (gene amplifications) were also obtained for our analysis.

The second dataset used for this analysis was obtained from Novartis NIBR-GNF (Cambridge MA) and the Harvard-MIT Broad Institute (Cambridge MA). This dataset included cell line growth inhibition datasets for 500+ cancer cell lines and 24 anti-cancer drugs, including DNA copy number variations obtained with Affymetrix SNP6.0 arrays and mRNA gene expression levels obtained with Affymetrix U133+2 arrays.

The third dataset used for this analysis was obtained from a recent study by Genentech (South San Francisco CA). This dataset included gene fusions, gene expression, and copy number variation for 675 cancer cell lines. Taken together, these three datasets have adhered to very strict guidelines for genotyping based identification of every cell line examined, thus avoiding any potential issues of cell line mislabeling or contamination that plagued past pharmacogenomics initiatives.

Statistical Significance of Clustering

Consider C genetically well-characterized cancer cell lines, on which 'cell growth inhibition assays' have been performed in a high throughput fashion with n drugs at varying concentrations (total of C × n experiments). The results of these dose response experiments are measures such as $IC_{50}$ (half-maximal inhibitory drug concentrations in natural log μM scale) and AUC (area under curve computed by curve-fitting data points). Our model transforms these measures into a new multidimensional vector space using a mechanistic transformation function. The synthesis of the transformation function is motivated by the biochemical sensitivity of drugs in living systems and their associated genetic characteristics (e.g., SNPs, insertions, deletions, gene amplifications, gene fusions, gene expression).

Each drug is a vector in the new multi-dimensional vector space (DrugSpace). This vector space's dimensions are picked based on a second multi-dimensional mutation vector space (MutationSpace). The whole exome of each cancer cell line is used to characterize the specific cell line in the mutational space.

The goodness of the DrugSpace can be assessed if some well-known similarity measures of the drug vectors (Euclidean distance, cosine similarity, etc.) correspond to some well-known drug behavior (phenotypic traits). We would also expect to see unrelated drugs to not score well on the pairwise similarity metric. More generically, we can ask whether there are collections of drugs that are "close" in some sense and hence form a cluster. If such clusters were distinct from other clusters, then the DrugSpace would have enabled us to discriminate different classes of drugs corresponding to different well known phenotypic traits.

Figure 10:
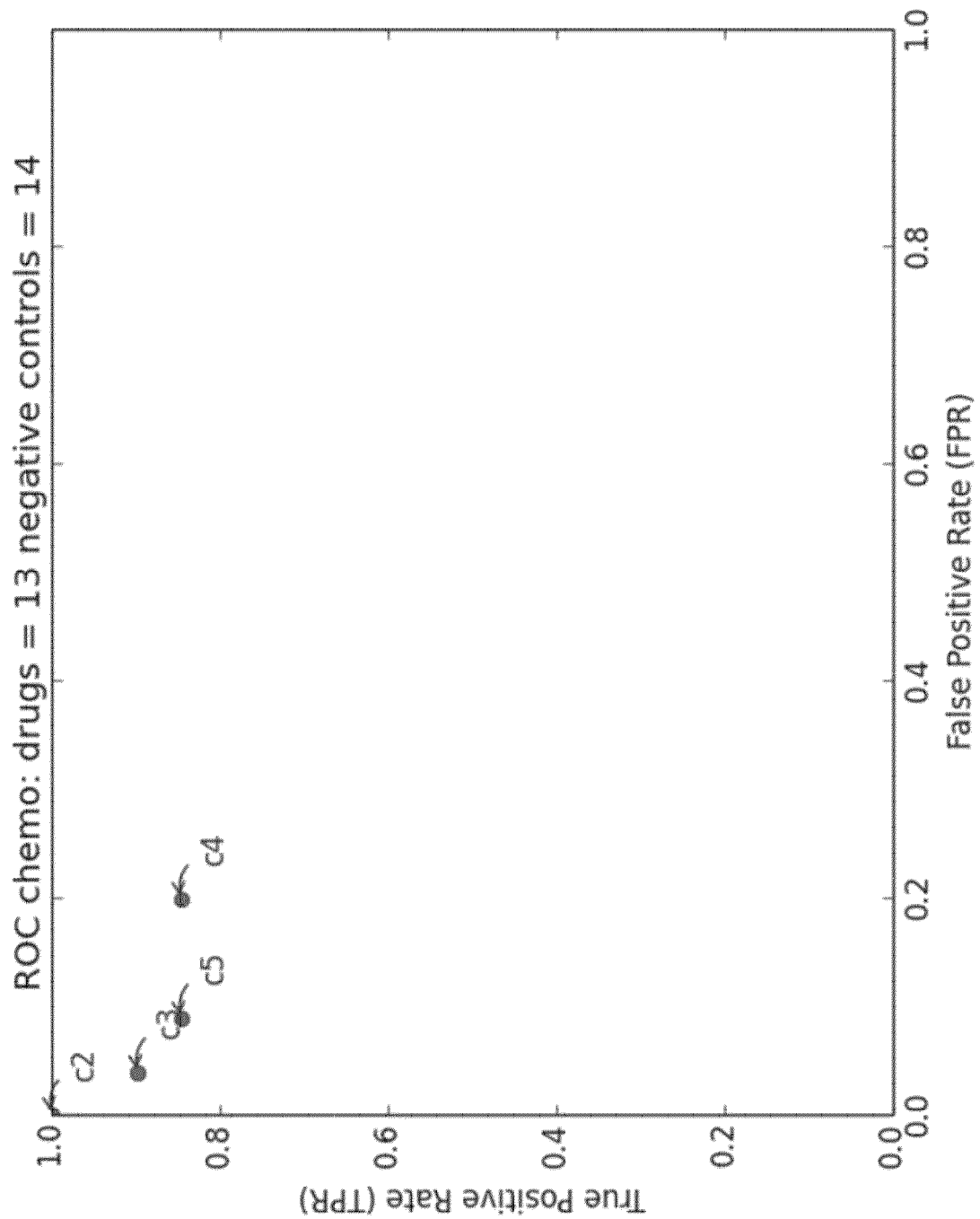
FIG. 10 is a scatter plot depicting the true positive and false positive rates for several exemplary clustering results.

We used a clustering algorithm (with number of clusters as the parameter) to study the emergent properties of the DrugSpace. There were 139 drugs under study of which we carved out a subset of 27 drugs that are FDA-approved cancer therapies. Of the 27 drugs, 13 were broadly cytotoxic (non-targeted) drugs and 14 were targeted cancer therapies (specifically targeting certain biomolecular pathways). We designed and tested a binary classifier of the DrugSpace which can classify a drug as either belonging to the broadly cytotoxic (non-targeted) class or the targeted therapy class. We used a small subset (k drugs out of 13) in the chemo therapy class to label every other drug in both the broadly cytotoxic (non-targeted) and the targeted therapy classes. In order to avoid any selection bias, every possible combination from the broadly cytotoxic (non-targeted) class was used as the training set to classify the remaining drugs, yielding a total of $\binom{13}{k}$ trials. The mean False Positive Rate (FPR) and mean True Positive Rate (TPR) were calculated and plotted on a Receiver Operating Characteristic (ROC) curve (FIG. 10). Here an illustration of the ROC curve is shown for not just the binary classifier (labeled c2) but also a pseudo binary classifier built from M-class classifiers (labeled c3-c5e).

Referring to FIG. 10, Perfect classification is obtained for the 2-cluster (c2) 2-class classification scheme – broadly cytotoxic (non-targeted) and non-broadly cytotoxic (non-targeted) drugs, with just one broadly cytotoxic (non-targeted) compound disclosed to the method. All drugs are iteratively cycled through as the one compound disclosed to the method while the other drugs are classified by our method. The p-value for observing this perfect classifier is 3.93e-13 (odds of ~ 4 in 10 trillion). The broadly cytotoxic (non-targeted) drugs used for this analysis are camptothecin, doxorubicin, docetaxel, mitomycin, bleomycin, vinorelbine, vinblastine, gemcitabine, etopiside, cisplatin, paclitaxel, methotrexate, and cytarabine. The non-chemotherapeutic (targeted) drugs used in this analysis are imatinib, nilotinib, ponatinib, bosutinib, dasatinib, crizotinib, erlotinib, gefitinib, afatinib, lapatinib, sunitinib, axitinib, sorafenib, and pazopanib.

The binary classifier is "perfect": it was able to classify every chemo drug as belonging to the chemo class (TPR = 1.0) and to classify every targeted drug as belonging to the non-chemo class (FPR = 1.0). The p-value for observing this result by chance is approximately 4 in 10 trillion (3.93e-12). The current rational oncology drug discovery paradigm of the pharmaceutical industry is focused on one or more specific molecular targets and generally not intended to be "broadly cytotoxic," but if a specific drug exhibits more promiscuous targeting properties (akin to broadly cytotoxic (non-targeted) drugs), we ought to be able to answer whether or not it will be specific by investigating whether the drug shares any "similarity traits" with the chemotherapeutic drugs. For this, it is helpful to increase the number of clusters in our clustering algorithm in order to gain a more nuanced and finer-grained picture of drug "similarity traits."

As the number of clusters is increased, we would generally expect fewer drugs per cluster and an increased probability of classification error for broad questions (e.g., is the drug a broadly-cytotoxic chemotherapeutic or more selectively targeted to a few biomolecules?). As a degenerate case, when the number of clusters is same as the total number of drugs, we would indeed have a TPR of 0 as none of the drugs will share a cluster with any training sample. For the chemotherapeutic vs. targeted therapeutic question, we can see from FIG. 10 the TPR range between 0.8-0.9 and FPR between 0.05-0.25. Despite the seemingly increased error rate for "broader" questions, the increase in clusters is actually useful for determining finer differences, such as which targeted cancer therapy drugs inhibit the same biochemical signaling pathway. That indeed is what we find for the ABL/SRC pathway targeted drugs vs. other drugs (FIG. 11).

Figure 11:
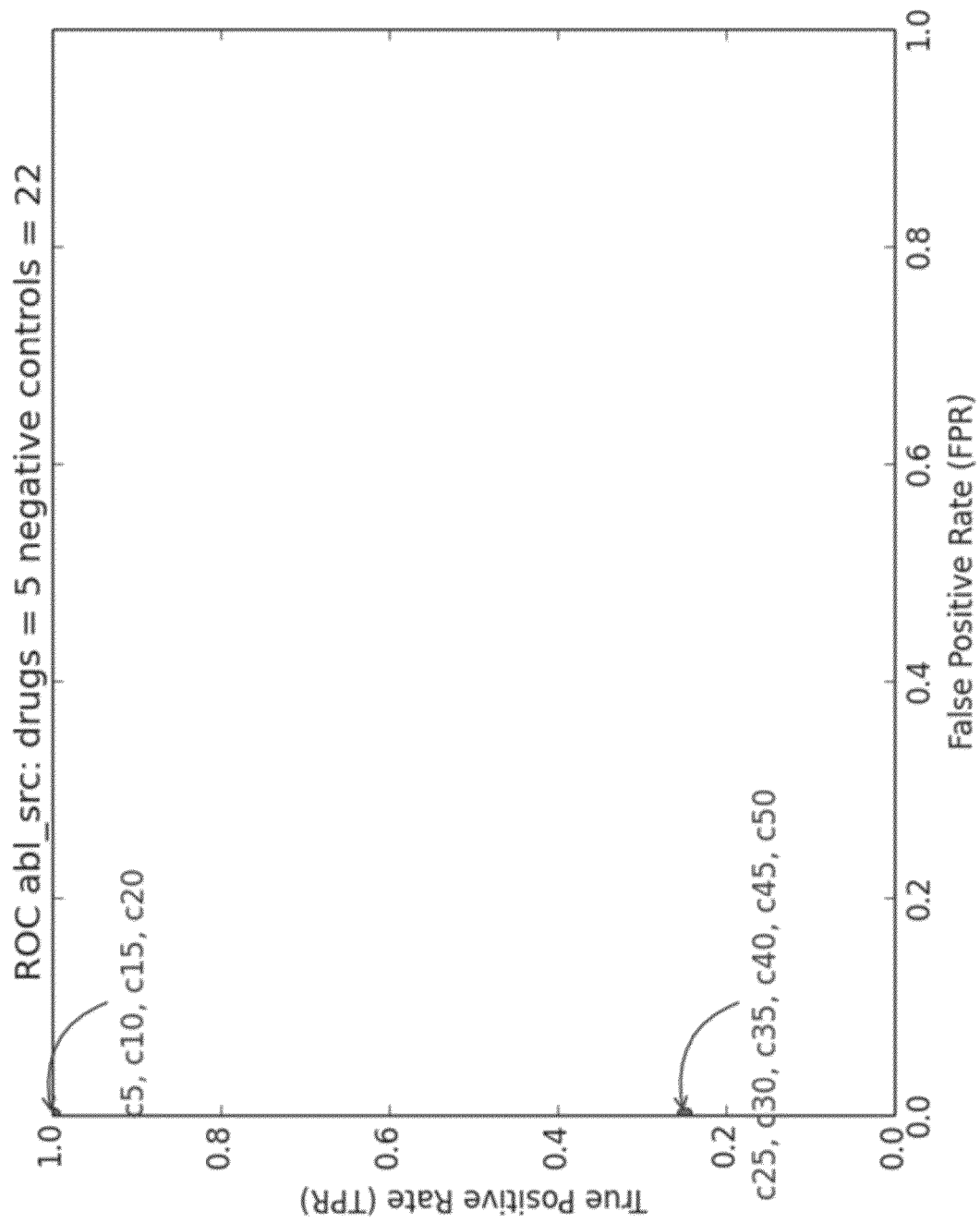
FIG. 11 is a scatter plot depicting the true positive and false positive rates for several exemplary clustering results.

Referring to FIG. 11, perfect classification is obtained for all classification schemes up to c20 (20 different clusters) for the 2-class classifier – targeted ABL/SRC pathway inhibitors and other drugs, with just one compound disclosed to the method from each class. All drugs are iteratively cycled through as the one compound disclosed to the method while the other drugs are classified by our method. The p-value for observing this perfect classifier is 3.93e-13 (odds of ~ 4 in 10 trillion). The ABL/Src drugs used for this test are imatinib, nilotinib, dasatinib, bosutinib, and AP.24534 (ponatinib), and the non ABL/Src drugs used are erlotinib, lapatinib, gefitinib, BIBW2992 (afatinib), PF.02341066 (crizotinib), axitinib, sorafenib, sunitinib, pazopanib, camptothecin, doxorubicin, docetaxel, mitomycin.C, bleomycin, vinorelbine, vinblastine, gemcitabine, etoposide, cisplatin, paclitaxel, methotrexate, and cytarabine.

Clusters c5-c20 remain perfect binary classifiers (TPR = 1.0 and FPR = 0.0). The p-value for observing this result by chance is approximately 3.93 in 10 trillion (4e-12). And as the cluster sizes increase (c25-c50), though the TPR is reduced to 0.25, the FPR stays at 0: more fine-grained properties are causing drugs to separate from a larger cluster without creating random mathematical artifacts. As an example, the drugs imatinib and nilotinib continue to belong to a "tight" cluster even at a larger number of clusters (such as a total of 30 clusters) while bosutinib has split off from the imatinib cluster but is still clustered with dasatinib (both of the latter drugs are ABL/Src kinase inhibiting drugs that are also multi-kinase targeted, in that they also act significantly on other distinct protein targets).

Figure 12:
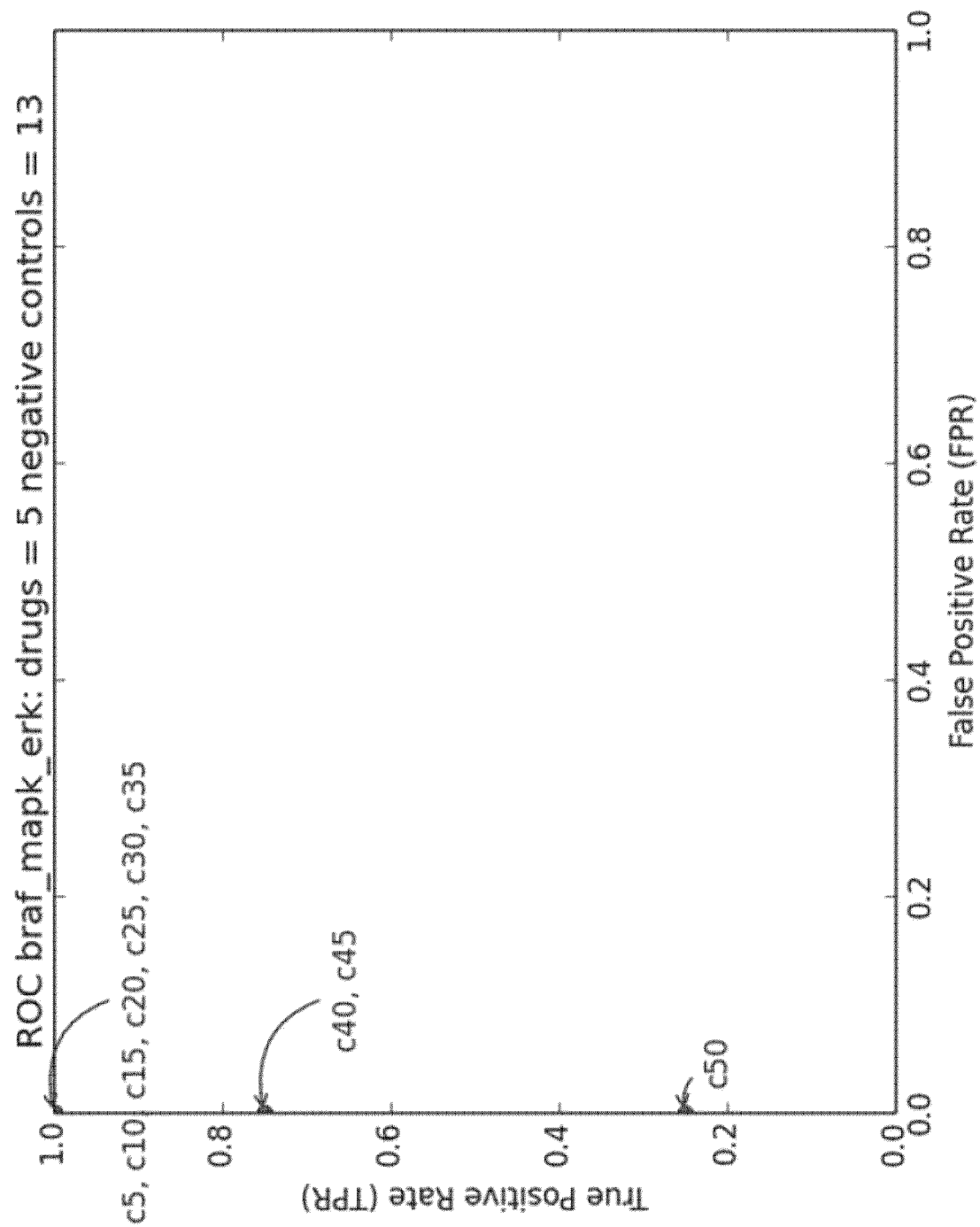
FIG. 12 is a scatter plot depicting the true positive and false positive rates for several exemplary clustering results.
Figure 13:
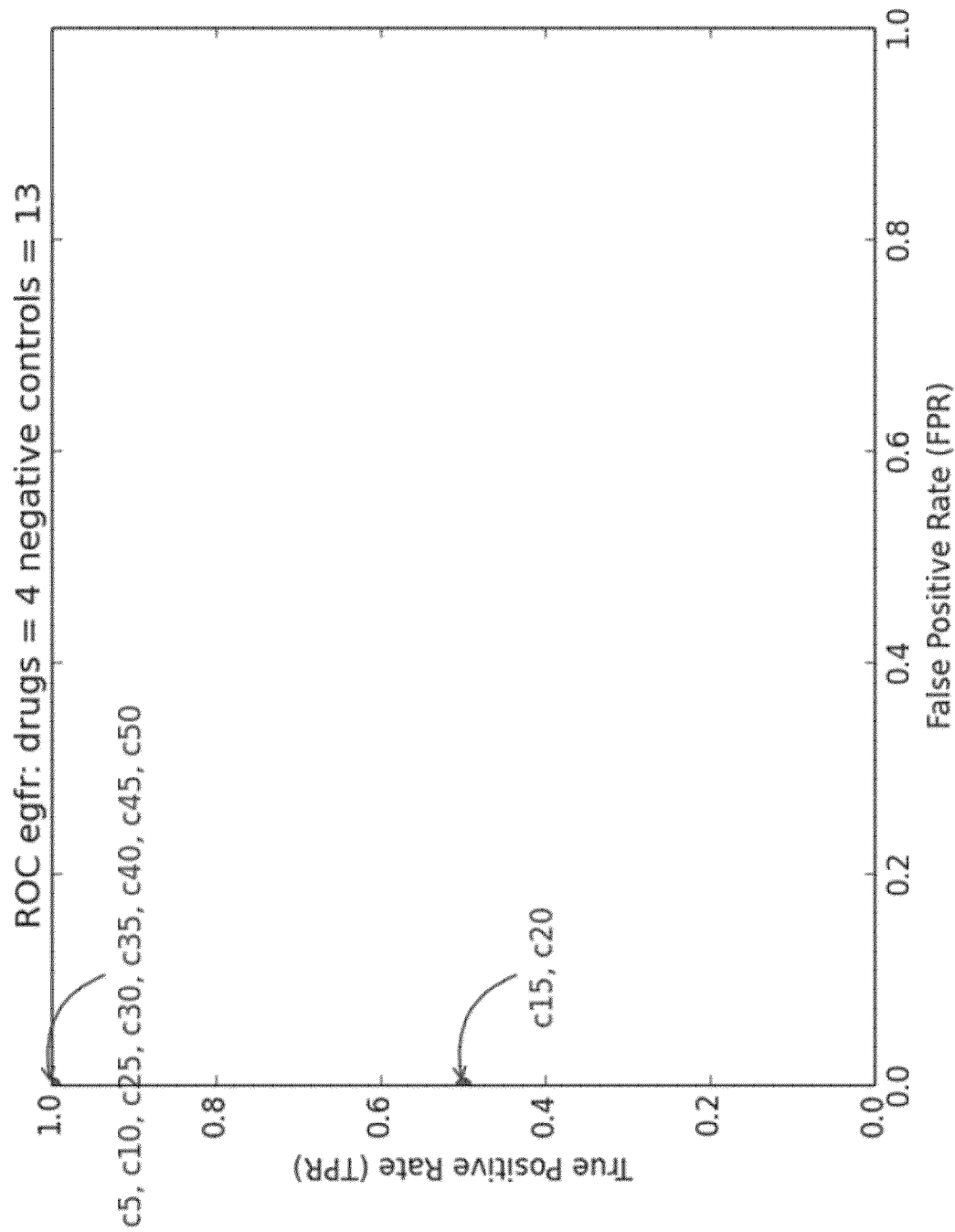
FIG. 13 is a scatter plot depicting the true positive and false positive rates for several exemplary clustering results.
Figure 14:
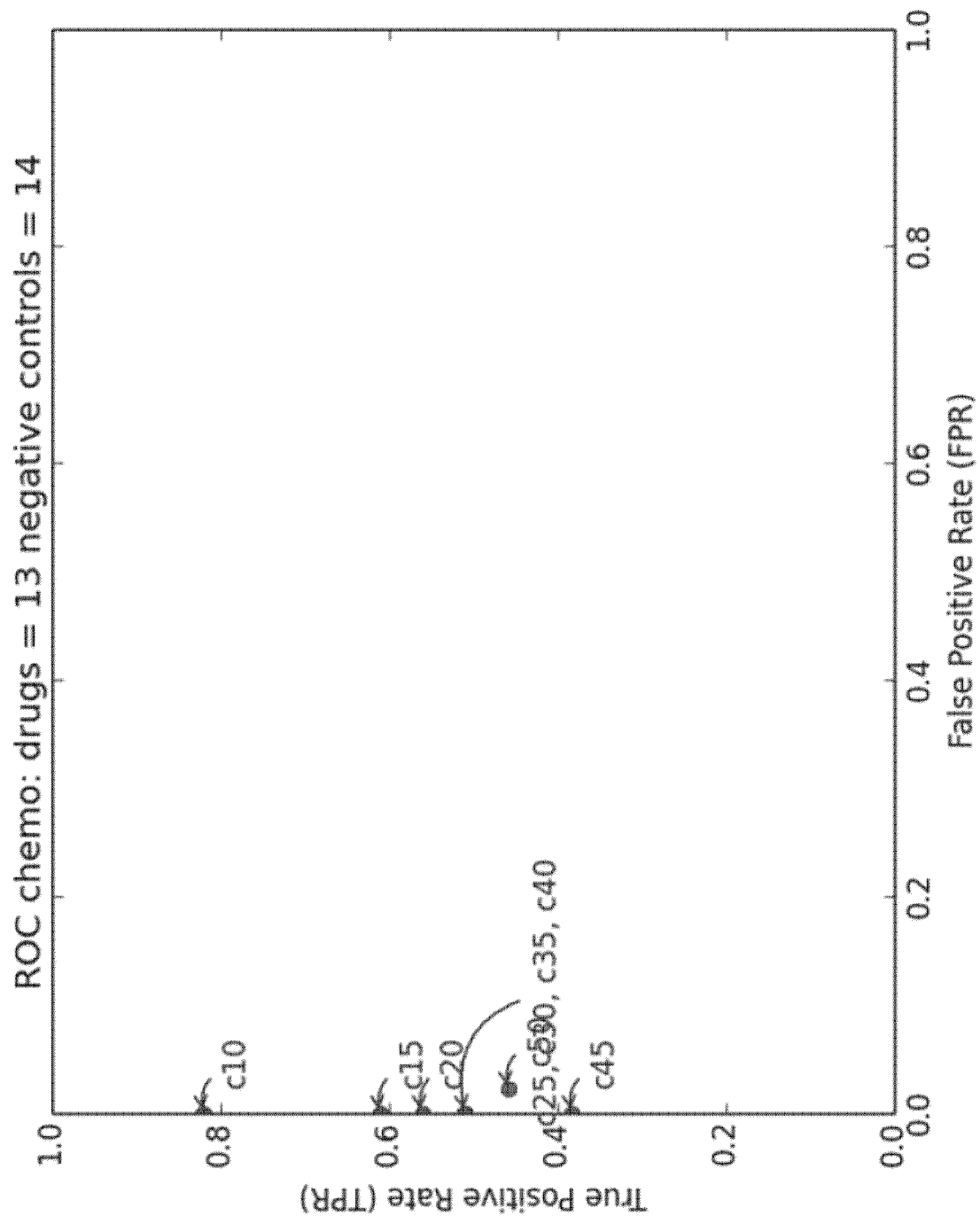
FIG. 14 is a scatter plot depicting the true positive and false positive rates for several exemplary clustering results.

FIGS. 12-14 depict the ROC results for three other pathways along with the drugs in the training set and negative controls. They demonstrate that as the number of clusters increase, finer grained properties of drugs cause the chemotherapy drugs to splinter (and hence the associated decrease in the True Positive Rate) but rarely does a broadly cytotoxic chemotherapy drug clusters with a known targeted drug. That is, our DrugSpace clustering algorithm has very low false positive rates (i.e., classifying a targeted drug as a chemotherapy drug).

FIG. 12 plots the BRAF-MAPK-ERK Drugs: vemurafenib (PLX4720), selumetinib (AZD6244), refametinib (RDEA119), SB590885, PD.0325901; and EGFR Drugs: erlotinib, lapatinib, gefitinib, afatinib (BIBW2992). The 13 chemotherapy drugs specified in FIG. 10 were used as negative controls.

FIG. 13 plots the EGFR pathway.

FIG. 14 shows how the FPR (a targeted drug being labeled as a chemotherapy drug) continues to be very low as the number of clusters increase. The worst case we see is only 1 error which translates to a FPR of less than 0.1; p-value = 6e-06 or 6 in a million when the number of clusters is 3. As the number of clusters increase, with the FPR held at the same value the probability of observing this result by chance diminishes to a vanishing 1.1e-21.

Equation (3) provides a measure of the classifiers' performance in aggregate:

$$rms = \frac{1}{n}\sum_{i=1}^{n}(TPR_i - FPR_i)^2 \qquad (3)$$

Figure 15:
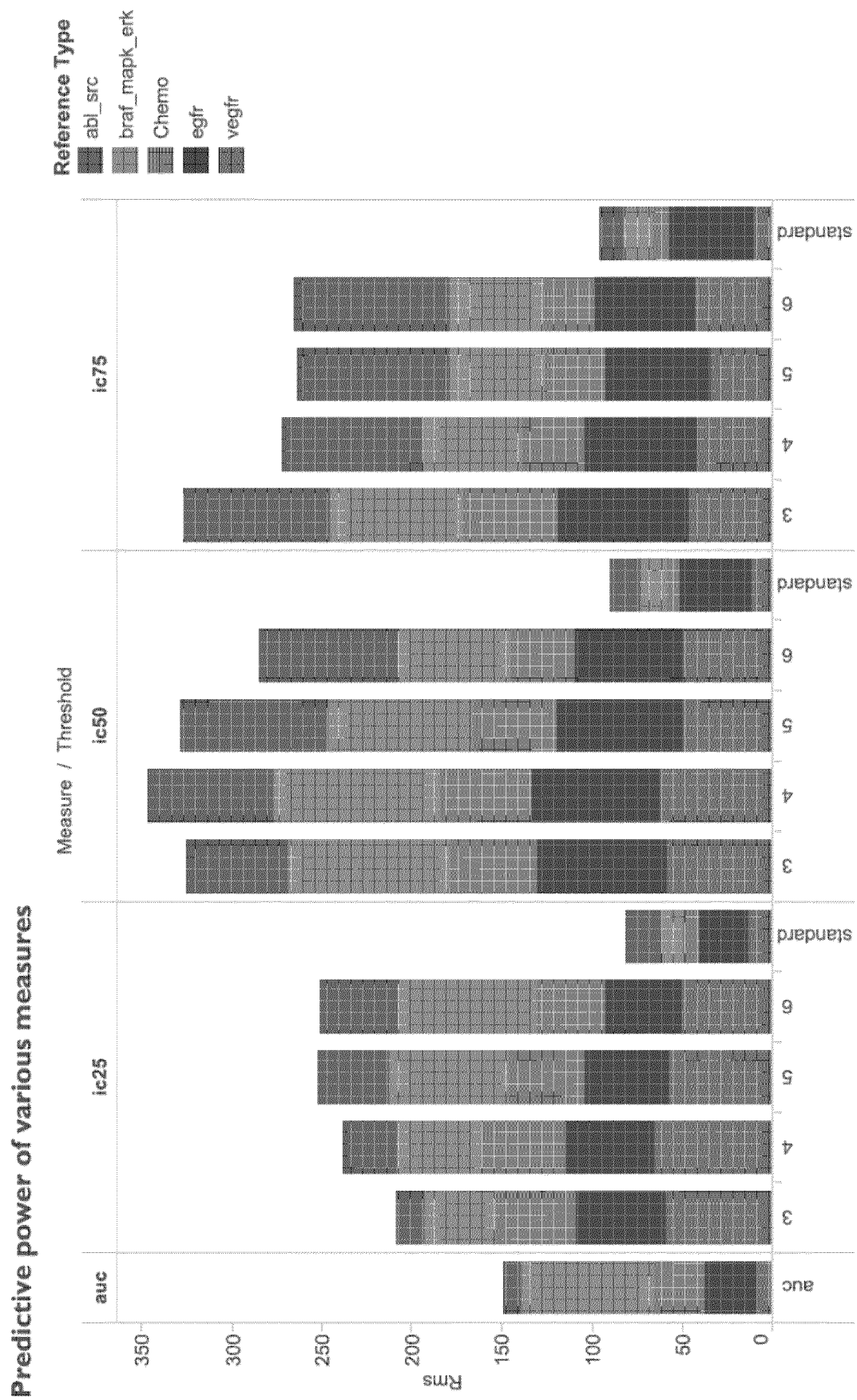
FIG. 15 is a bar graph depicting a measurement of classification performance for several exemplary clustering results.

Noting that the n-ary classifier's output was converted to that of a binary classifier by grouping multiple clusters into just two clusters (one cluster which corresponds to the set of reference drugs and another corresponding to the drugs that are different from the reference drugs in certain metric: such as broadly cytotoxic vs. targeted classes), FIG. 15 illustrates the sensitivity of the binary classifier's performance to the number of clusters (n). FIG. 15 shows the sum of rms of each classifier's performance for transformed measures at various threshold parameters (standard ic25, ic50, ic75, and auc measures are shown as well). Various binary classifiers are shown in shading.

Figure 16:
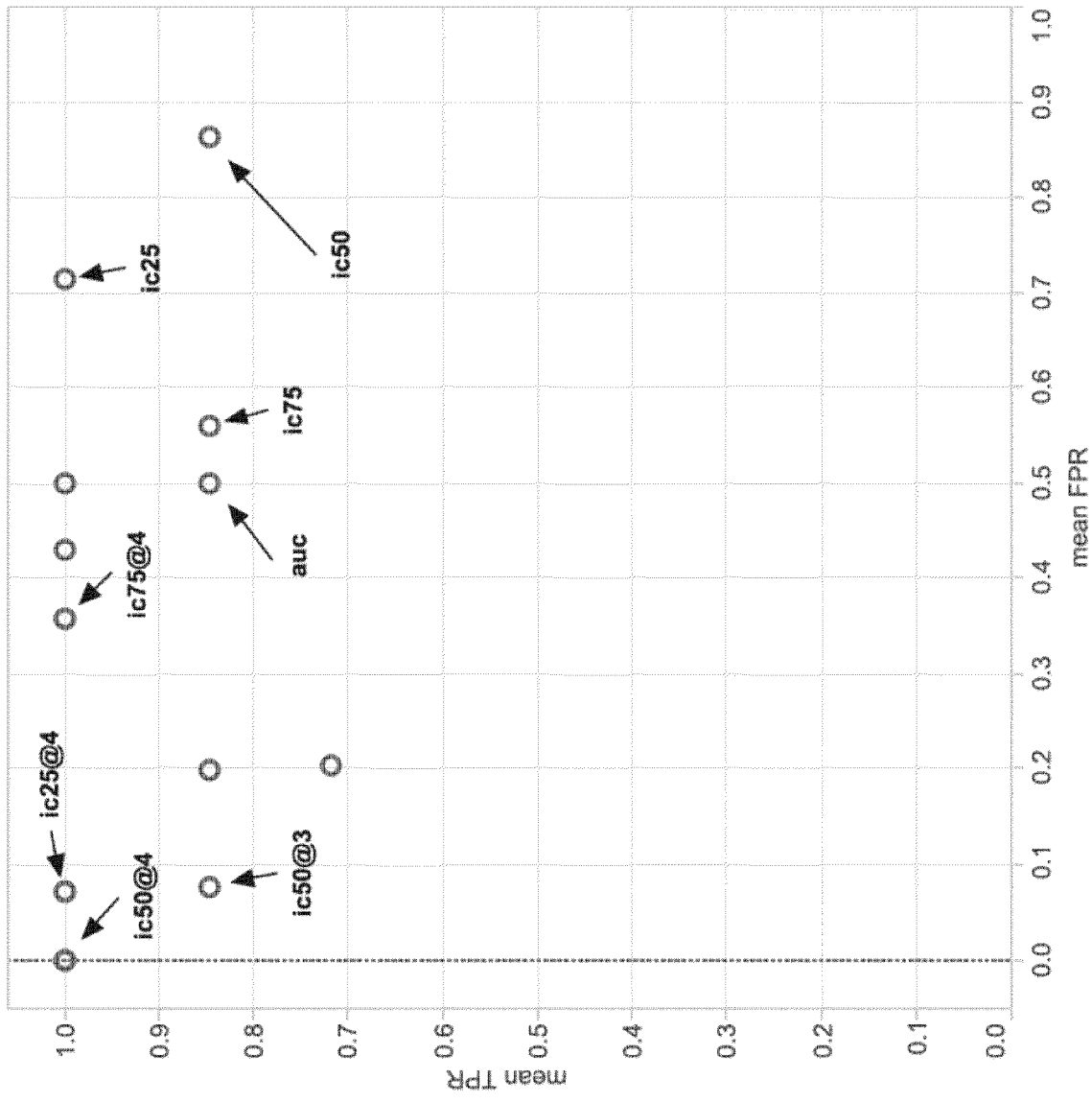
FIG. 16 is a scatter plot depicting the true positive and false positive rates for several exemplary clustering results.
Figure 17:
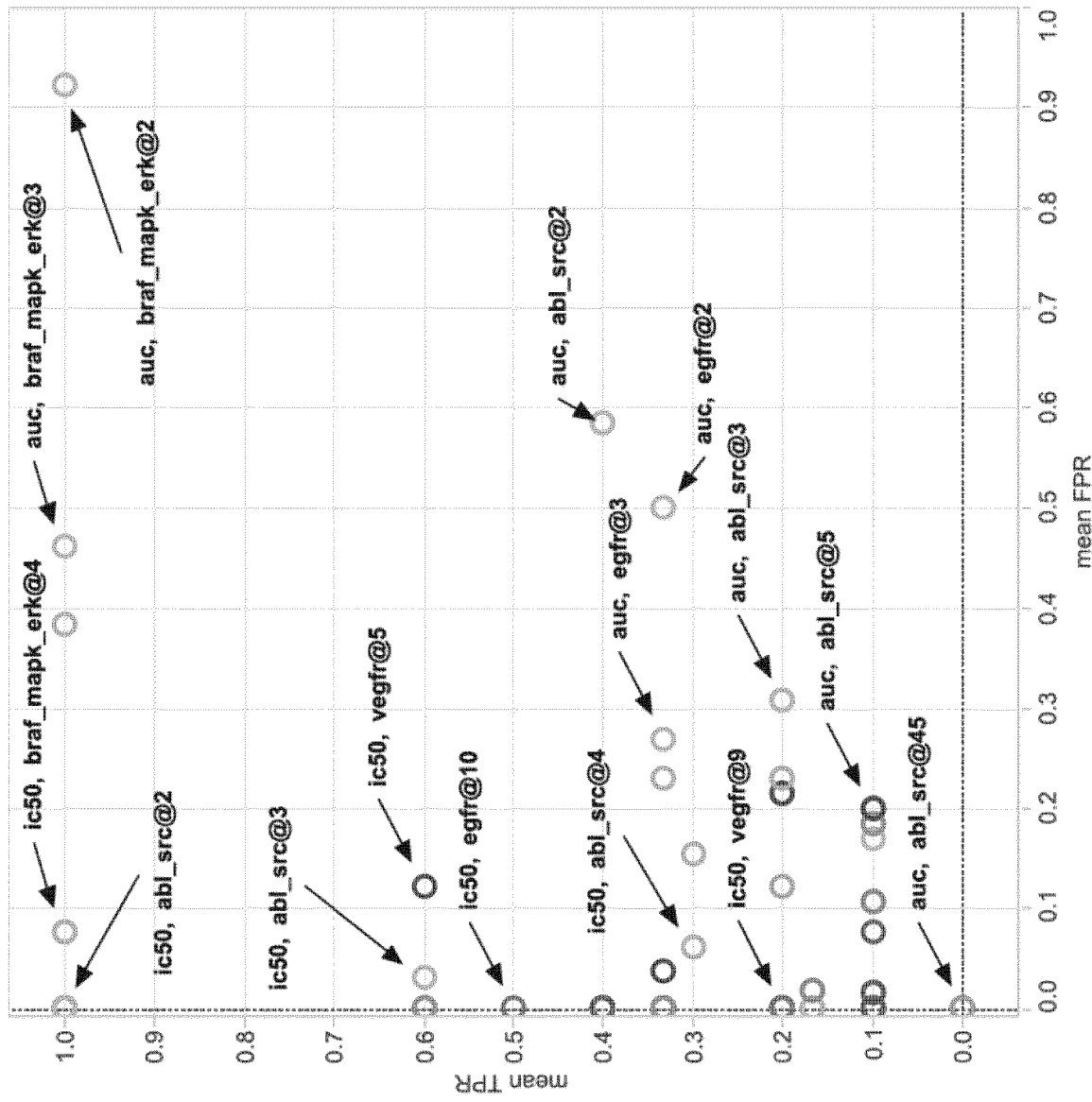
FIG. 17 is a scatter plot depicting the true positive and false positive rates for several exemplary clustering results.

FIGS. 16-17 shown mean false positive rate (FPR) versus mean true positive rate (TPR) for various targeted classifiers at various cluster sizes for the two measures: transformed 1c50 and auc. The auc measure is susceptible to high FPR independent of the cluster sizes. The transformed ic50 measure's TPR decreases as expected for larger cluster sizes while keeping the FPR low.

In ROC curves such as those depicted in FIGS. 16-17, there is one point ($FPR_i$, $TPR_i$) corresponding to each ($i^{th}$) classifier's performance. The point on the top extreme left of the plot (0,1) corresponds to a perfect classifier with 100% True Positive Rate (TPR) and 0% False Positive Rate (FPR). The points that lie on the 45° line (y = x) do not provide any useful classification since the TPR and FPR are equal (one could obtain the same result with a coin toss, for example). The more distant a point is from the 45° line (y = x) is, the better the corresponding classifier's performance. The aggregate performance of a group of classifiers (in our case, each classifier that we obtained by varying the number of clusters) is then the average of the deviations to the 45° line (each deviation is just the altitude of the point with respect to the line y = x). The higher the value of rms (root mean square deviation provided by Equation (3), the better the aggregate performance of the classifiers. We express the rms value calculated this way in a scale ranging from 0 to 100 where 0 corresponds to the worst aggregate performance and 100 corresponds to the best aggregate performance.

While the single parameter rms can be useful in distinguishing between classifiers, choice of the classifier may of course be also or alternatively based on a combination of other factors.

There is thus information to be gleaned as the number of clusters increases. Typically this information gives a clue to some molecular similarity of the underlying targets that the drugs are inhibiting. Resulting hypotheses may then be subjected to a more focused and thorough experimental validation.

Imatinib Results

Imatinib is an FDA-approved blood cancer drug that inhibits the BCR-ABL1 gene fusion by acting on the ABL1 protein kinase domain. The method described herein classifies imatinib, nilotinib, and GNF-2 together for 30 total clusters using the transformed values from the raw $IC_{50}$ values as well as the area under the dose response survival curves (AUC) (FIG. 18).

Figure 18:
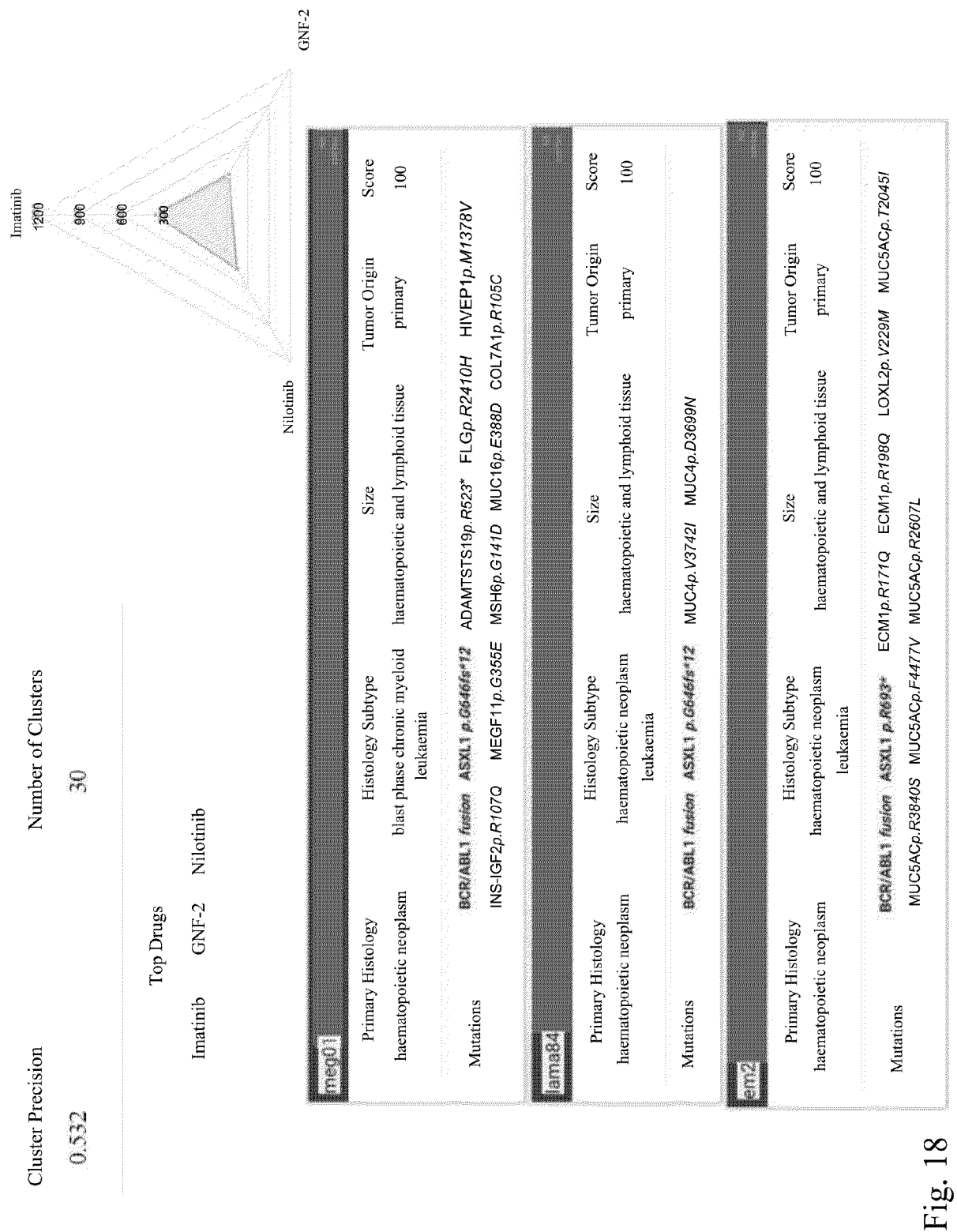
FIG. 18 depicts an exemplary screenshot of output describing a cluster of drugs.

Referring to FIG. 18, the imatinib cluster at total number of clusters of 30 is shown. The genetics of the most significant cell line dimensions contributing to this cluster are also shown (LAMA-84, MEG-01, EM-2), highlighting the shared co-occurring genetic traits of BCR/ABL1 fusion and the ASXL1 truncation.

Figure 23:
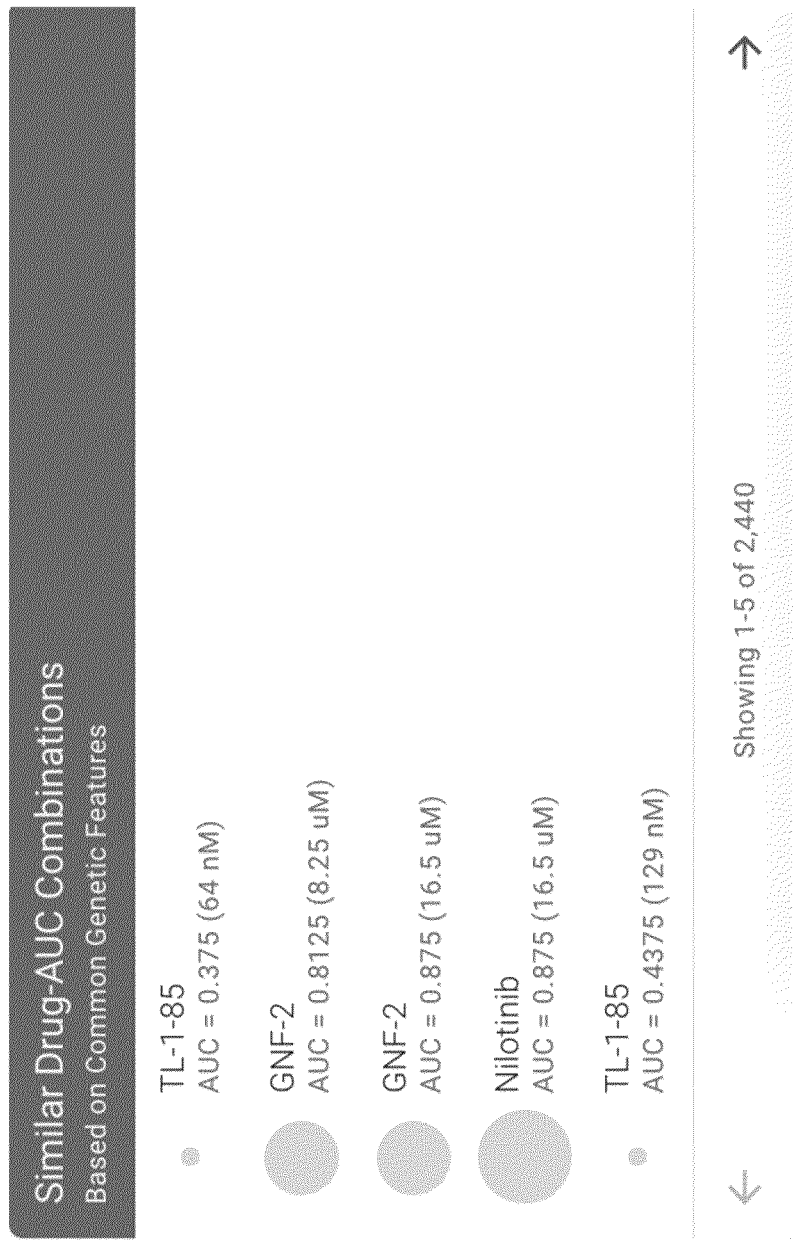
FIG. 23 depicts exemplary output of similar drug-AUC combinations according to embodiments of the present disclosure.

Exemplary output of similar drug-AUC combinations based on common genetic features is illustrated in FIG. 23.

The BCR-ABL1 gene fusion occurs in a significant majority of cell lines that are the most salient dimensions contributing to this cluster (p-value = 8.35E-09), including the LAMA-84, EM-2, and MEG-01 cell lines (FIG. 19). Thus, the BCR-ABL1 gene fusion emerges as a shared genetic trait for the cell lines contributing to the imatinib drug cluster. In addition to the BCR-ABL gene fusion, ABL1 gene over-expression is also a significant signal (p-value = 1.45E-04). Further, gene fusions such as NUP214-ABL and Rhe-PDGFRα that appear in one of the cell lines that are "most significant dimensions" for the imatinib cluster emerge as insignificant signals (p-value > 0.2). Incidentally, imatinib, nilotinib, and GNF-2 have been shown to also inhibit the ABL1 kinase domain of the NUP214-ABL fusion protein and the kinase domain of the PDGFRα protein as secondary targets.

Figure 24:
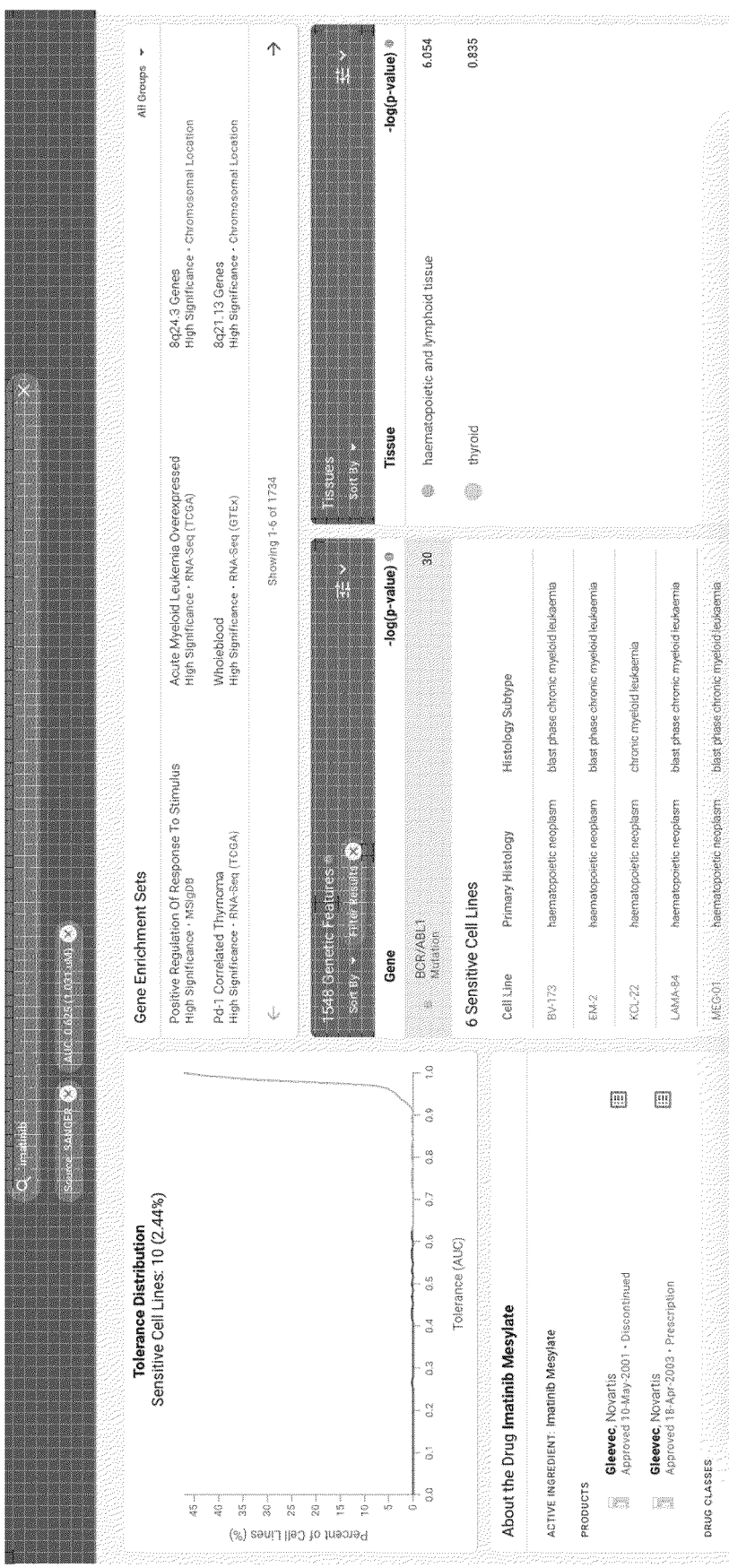
FIG. 24 depicts exemplary output of tolerance distribution, gene enrichment sets, genetic features, and tissues corresponding to imatinib according to embodiments of the present disclosure.

Exemplary output of tolerance distribution, gene enrichment sets, genetic features, and tissues corresponding to imatinib is illustrated in FIG. 24.

FIG. 19 is a table showing co-occuring BCR-ABL1 fusion and ASXL1 truncation genetic trait in imatinib cluster.

The co-occurrence of the BCR-ABL gene fusion and the ASXL1 gene truncation is a novel and significant signal from the imatinib cluster (FIGS. 11, 19). Incidentally, ASXL1 gene truncations have recently been implicated in clinical studies as a modulator of imatinib efficacy. Additionally, we observe statistically significant co-occurrence of BCR-ABL gene fusion with SOCS2 over-expression (p-value = 6.6E-06), EIF3E over-expression (p-value = 1.3E-03), GAB2 over-expression (p-value = 1.3E-03), and FH under-expression (p-value = 2.1E-03), which are all transcriptional signals. SOCS2 gene over-expression has been linked in multiple preclinical and clinical settings as a key modulator of imatinib (STI-571) efficacy.

We next tested the classification of imatinib with other drugs for the raw $IC_{25}$ values. The concentration of compound required for 50% growth inhibition of cell cultures ($IC_{50}$) is always larger than the concentration of compounds required for 25% growth inhibition ($IC_{25}$). The previous classification of compounds (above) was based on the raw $IC_{50}$ values, which represents inhibitory phenotypic effects for a "larger concentration" of compound. We wanted to compare this with inhibitory phenotypic effects for a "smaller concentration" of compound. Specifically, we wanted to compare the genetic and transcriptional signals significantly associated with the "larger concentration" of compound with those significantly associated with the "smaller concentration" of compound.

Our cluster explorer method classifies imatinib with axitinib, nilotinib, AP.24534 (ponatinib), and pazopanib for 30 total clusters using the transformed values from the raw $IC_{25}$ values. While BCR/ABL gene fusion is still a significant biomarker (p-value = 4.7E-09), and ABL1 overexpression is still a significant biomarker (p-value = 1.7E-03), there are new significant biomarkers such as PDGFRA overexpression (p-value = 4.4E-03) and FGFR1 over expression (p-value = 3.5E-03), which appear from the $IC_{25}$ analysis but not the $IC_{50}$ analysis. Thus, biomarkers such as PDGFRA overexpression and FGFR1 overexpression, which are both known clinical correlates of imatinib activity in vivo,[16,17] appear more closely associated to imatinib at lower drug concentrations than at higher drug concentrations. On the other hand, other significant biomarkers such as MAPK1 overexpression are slightly more significant at higher imatinib concentrations (from $IC_{50}$ computation) than at lower imatinib concentration (from $IC_{25}$ computation), with p-values of 3.8E-04 and 4.3E-03 respectively. This is in contrast to another significant biomarker MAPK14 (p38α kinase) for which overexpression is relatively similar at higher imatinib concentrations (from $IC_{50}$ computation) than at lower imatinib concentration (from $IC_{25}$ computation), with p-values of 1.6E-04 and 1.5E-04 respectively. Both MAPK1 and MAPK14 have been implicated in modulating imatinib efficacy in both in-vitro systems and in the clinic. These insights provide mechanistic biomarkers for deducing minimum effective dosage and maximum tolerable dosage in clinical trial therapeutic regimen.

Next, we examined potential inflammatory biomarkers that emerge from our analysis at both $IC_{50}$ and $IC_{25}$ based computations. We find that IL3RA over-expression is the only significant biomarker of inflammation that emerges for the imatinib cluster, with p-values of 1.7E-03 (for $IC_{25}$) and 9.9E-03 (for $IC_{50}$).

Likewise, we also find a few significant biomarkers of immuno-modulation and cardiac function for the imatinib cluster from $IC_{50}$ computations. These include PRSS57 over expression (p-value = 2E-08), CSF2RB over expression (p-value = 1.4E-03), AZU1 over expression (p-value = 1.5E-03), and CELA1 over expression (p-value = 5.6E-03). We also find a very significant biomarker of cardiac function, namely KCNH2 over expression (p-value = 1.4E-03), where KCNH2 belongs to the potassium ion channel family of genes that plays a critical role in QT generation of cardiomyocytes from heart tissues. Additional cardiac function biomarkers that are somewhat significant include REG3G over expression (p-value = 6.2E-03) and FADS2 over expression (9E-03).

FIG. 20 is a table showing Oncogenes that are transcriptionally associated significantly with the imatinib cluster (from $IC_{50}$ computations using total clusters of 30).

Next we examined all known oncogene biomarkers that emerge from the imatinib drug cluster from $IC_{50}$ computations at 30 total clusters (FIG. 20). In addition to those oncogenes that we have already mentioned, there are numerous important oncogenes, whose transcription levels appear statistically coupled with the imatinib cluster, including over-expression of LYL1, STAT5B and STAT5A, CSF3R and CSF1R, and MAPK14 and MAP3K7.

Crizotinib Results

Figure 25:
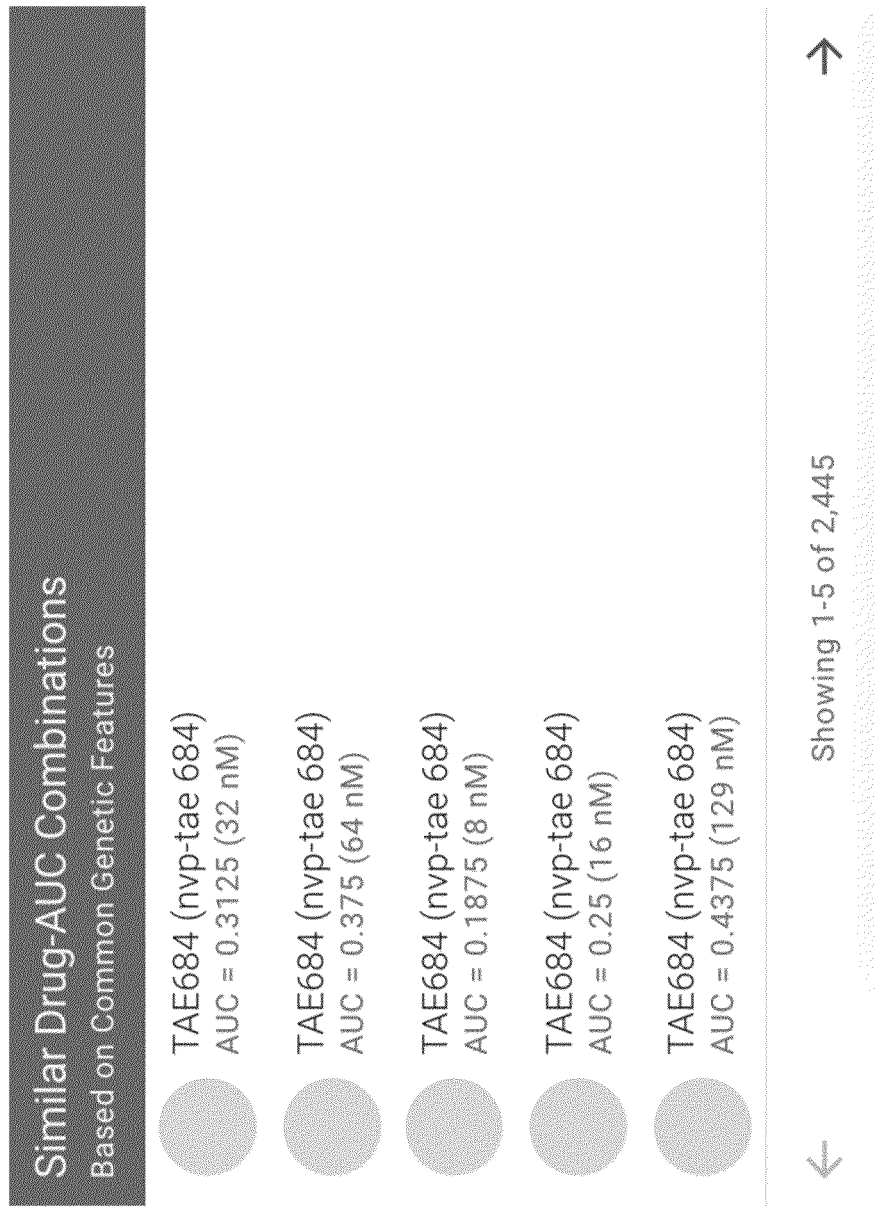
FIG. 25 depicts exemplary output of similar drug-AUC combinations according to embodiments of the present disclosure.

We find that crizotinib (PF.02341066) and NVP-TAE684 cluster together at 30 total number of clusters for the $IC_{50}$ based computation. Exemplary output of similar drug-AUC combinations based on common genetic features is illustrated in FIG. 25.

Incidentally, both crizotinib and NVP-TAE684 are known to be targeted to ALK gene fusions such as EML4-ALK gene fusion. ALK over expression has a very significant p-value pf 2.31E-08 and occurs in 6 of the 8 cell lines that constitute the most significant dimensions for the crizotinib cluster. This is the first signal to emerge from our method that has clinical validation. Additionally, we find that the gene fusions ALK/GALNT14, ALK/SCEL, DDX6/ALK EML4/ALK, GTF21RD1/ALK, and STRN/ALK all have a very significant p-value of 6.7E-06. The gene fusions SMEK2/ALK, TPM1/ALK, and TPM3/ALK all have very significant p-value of 1.2E-05, while the gene fusion NPM1/

ALK has p-value of 1.1E-04. Validating our predictions, we find that every one of these ALK genetic alterations have been clinically observed as determinants of crizotinib drug efficacy.

Figure 26:
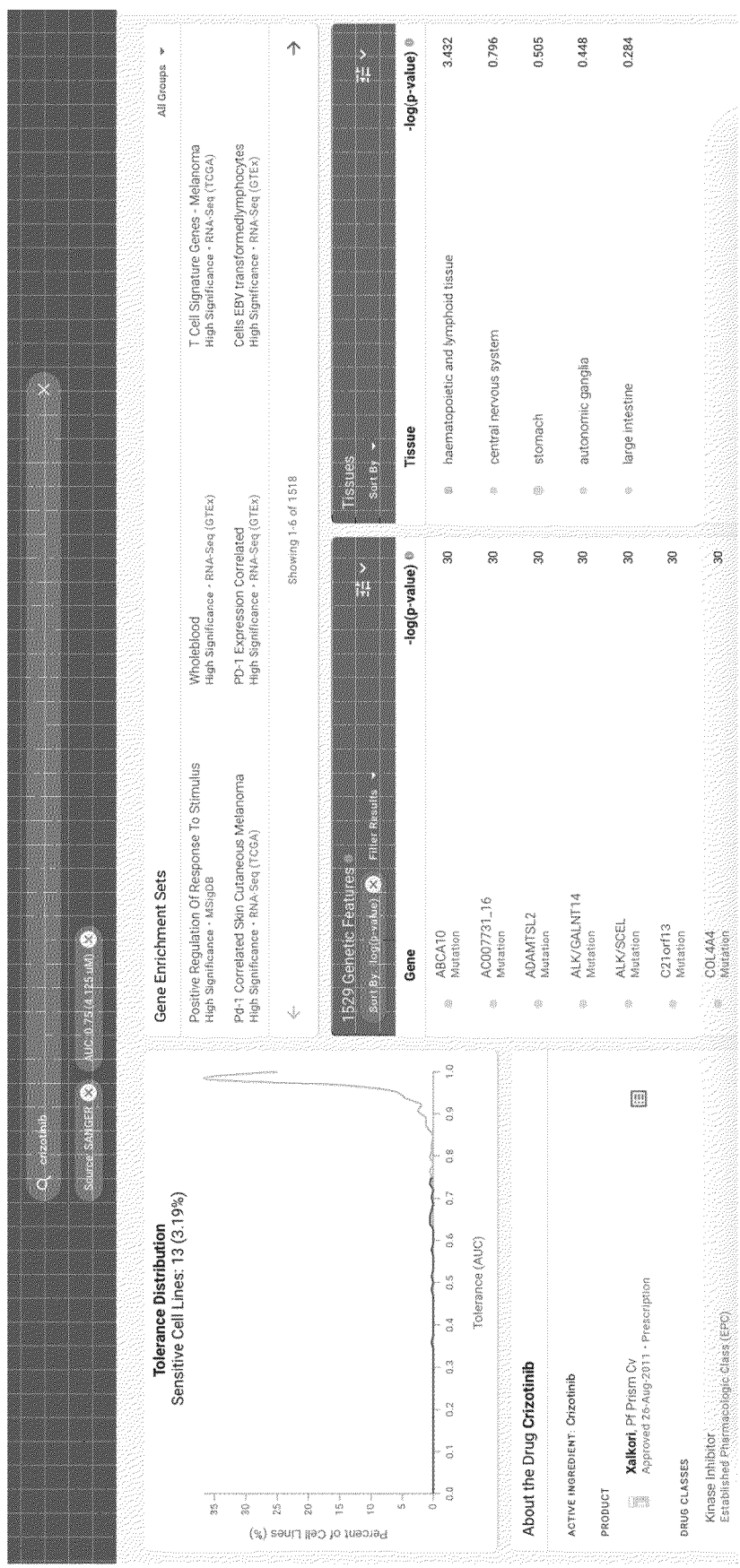
FIG. 26 depicts exemplary output of tolerance distribution, gene enrichment sets, genetic features, and tissues corresponding to crizotinib according to embodiments of the present disclosure.

Exemplary output of tolerance distribution, gene enrichment sets, genetic features, and tissues corresponding to crizotinib is illustrated in FIG. 26.

FIG. 21 is a table showing Status of ALK mutations, ALK expression level, and ALK amplification for most significant cell lines of the crizotinib drug cluster at 30 total number of clusters.

The most significant cell line dimensions contributing to the crizotinib cluster are, in decreasing order of dimensional salience, NB1, SR, SF539, SCC-3, DEL, NCI-SNU-5, KARPAS-200, and SU-DHL1 (FIG. 21). We find that NB1 has a significant ALK gene amplification (copy number of 14), whereas NB1, SR, SCC-3, DEL, KARPAS-299, and SU-DHL-1 have significant ALK gene over-expression. Further, SR, SCC-3, and SU-DHL-1 have multiple ALK fusions with other genes, including TFG-ALK, EML4-ALK, DDX8-ALK, GALNT14-ALK, SCEL-ALK, SMEK2-ALK, STRN-ALK, GTF2IRD1-ALK, TPM1-ALK, and TPM3-ALK gene fusions. Finally, randomly selected other cell lines that are not part of the most significant cell line dimensions, such as 639v, HCE-4, and NCI-H1299 do not have any of the ALK gene modifications. Most significant cell line dimensions contributing to the crizotinib cluster thus have significant on-target genetic modifications that emerge from our biological-hypothesis-free cluster explorer method. Of course, these are much more comprehensively captured by the p-value computations for each genetic variation.

Next, we examined potential inflammatory biomarkers that emerge from our analysis at both $IC_{50}$ and $IC_{25}$ based computations. Unlike imatinib (where there was hardly any inflammatory biomarker), we find IL18RAP over-expression (p-value = 7.2E-07), IL1R2 over-expression (p-value = 2.7E-06), IL26 over-expression (p-value = 3.2E-07), IL2RA over-expression (p-value = 8.7E-07), and IL4E over-expression (p-value = 2E-06) in the crizotinib cluster. All are very significant inflammatory biomarkers of the interleukin family.

Likewise, we also find a few significant biomarkers of immuno-modulation and cardiac function for the crizotinib cluster from $IC_{50}$ computations. These include GZMB over-expression (p-value = 7.2E-07), NKG7 over-expression (p-value = 3.6E-06), PRF1 over-expression (p-value = 2.5E-07), and GZMA over-expression (p-value = 3.3E-04). We also find a biomarker of cardiac function, namely TIMP1 over-expression (p-value = 9.6E-06).

FIG. 22 is a table showing oncogenes significantly associated with the crizotinib drug cluster at 30 total clusters computed from the $ic_{50}$ values.

In addition to the above genes, we next surveyed the key oncogenes associated with the crizotinib drug cluster from the $IC_{50}$ computations (FIG. 22). Few selected oncogenes whose transcriptional levels are significantly over expressed in the crizotinib cluster include TNFRSF8, Janus Kinase 3 (JAK3), STAT5B, CSF1R, CD274, PDE4DIP and PDE4D.

While various embodiments of the present disclosure have been shown and described herein, it will be obvious to those skilled in the art that such embodiments are provided by way of example only. Numerous variations, changes, and substitutions will now occur to those skilled in the art without departing from the disclosure. For example, cluster engine 600 may perform calculations based on assay data previously stored in compound database 608 rather than data received from an assayer 504. It should be understood that various alternatives to the embodiments of the disclosure described herein may be employed in practicing the disclosure. Elements of an implementation of the systems and methods described herein may be independently implemented or combined with other implementations. It is intended that the following claims define the scope of the disclosure and that methods and structures within the scope of these claims and their equivalents be covered thereby.

What is claimed is:

1. A computer-implemented method of predicting phenotypic relatedness of pharmaceutical compounds, the method comprising:
    determining a plurality of vectors associated with a plurality of pharmaceutical compounds, wherein the plurality of pharmaceutical compounds are cancer inhibitory drugs, and wherein
        each of the plurality of vectors is associated with one of the plurality of pharmaceutical compounds,
        each of the plurality of vectors has a plurality of components,
        each of the plurality of components is associated with one of a plurality of reagents, and
        each of the plurality of components of each of the plurality of vectors is based on a functional interaction between its associated reagent and the compound associated with its vector;
    transforming each of the plurality of vectors by applying a transformation function to each component of each vector;
    identifying at least a first and a second cluster of the plurality of pharmaceutical compounds based on the transformed plurality of vectors, wherein the identified first and second clusters each include at least one contributing cell line dimension;
    selecting an inhibitory drug from the identified first and second clusters based on a genetic trait of the contributing cell line dimension;
    conducting a drug-patient matchmaking based on the genetic trait to thereby select a patient; and
    administering the selected inhibitory drug to the selected patient.

2. The method of claim 1, further comprising identifying a subset of reagents based on vector components that are associated with the first cluster.

3. The method of claim 2, further comprising identifying at least one biomarker associated with the subset of reagents.

4. The method of claim 3, wherein the at least one biomarker is associated with a drug target.

5. The method of claim 3, wherein the at least one biomarker is associated with a drug pathway of mechanism.

6. The method of claim 3, wherein the at least one biomarker is associated with deleterious toxicity.

7. The method of claim 3, wherein the at least one biomarker is associated with an immunomodulatory signal.

8. The method of claim 1, further comprising identifying at least one functional property associated with the subset of reagents.

9. The method of claim 1, wherein the first and the second clusters are identified based on distances between vectors associated with each pharmaceutical compound in the first cluster and distances between vectors associated with each pharmaceutical compound in the second cluster.

10. The method of claim 1, further comprising:
    normalizing each vector in the plurality of vectors; and applying the k-means clustering algorithm to the plurality of normalized vectors.

11. The method of claim 1, wherein each reagent in the plurality of reagents is a mammalian cell line.

12. The method of claim 11, wherein each mammalian cell line is a cancer cell line.

13. The method of claim 1, wherein each reagent in the plurality of reagents is a protein.

14. The method of claim 13, wherein each protein in the plurality of reagents is a cell receptor.

15. The method of claim 13, wherein each protein in the plurality of reagents is an enzyme.

16. The method of claim 15, wherein each enzyme in the plurality of reagents is a kinase.

17. The method of claim 1, wherein at least one functional interaction is half-maximal inhibitory concentration ($IC_{50}$).

18. The method of claim 1, wherein at least one functional interaction is half-maximal effective concentration ($EC_{50}$).

19. The method of claim 1, wherein at least one functional interaction is area under the curve (AUC).

20. The method of claim 1, wherein a first component of a first vector in the plurality of vectors is associated with a first functional interaction of a first compound with a reagent in the plurality of reagents, and a second component of the first vector is associated with a second functional interaction of the first compound with the reagent.

21. The method of claim 1, further comprising:
appending to each of the plurality of transformed vectors at least one literature-derived score, the at least one literature-derived score representing an association between an associated compound and a corresponding reagent within literature.

22. A computer-implemented method of predicting phenotypic relatedness of pharmaceutical compounds, the method comprising:
determining a plurality of vectors associated with a plurality of pharmaceutical compounds, wherein the pharmaceutical compounds are cancer inhibitory drugs, and wherein
each of the plurality of vectors is associated with one of the plurality of pharmaceutical compounds,
each of the plurality of vectors has a plurality of components,
each of the plurality of components is associated with one of a plurality of reagents, and
each of the plurality of components of each of the plurality of vectors is based on a functional interaction between its associated reagent and the compound associate with its vector;
normalizing each of the plurality of vectors;
identifying at least a first and a second cluster of the plurality of pharmaceutical compounds based on the normalized plurality of vectors, wherein the identified first and second clusters each include at least one contributing cell line dimension;
selecting an inhibitory drug from the identified first and second clusters based on a genetic trait of the contributing cell line dimension;
determining a biomarker of the at least one significant cell line of the first and second clusters;
conducting a drug-patient matchmaking based on the genetic trait to thereby select a patient; and
administering the selected inhibitory drug to the selected patient.

23. The method of claim 22, further comprising identifying a subset of reagents based on vector components that are associated with the first cluster.

24. The method of claim 23, further comprising identifying at least one biomarker associated with the subset of reagents.

25. The method of claim 24, wherein the at least one biomarker is associated with a drug target.

26. The method of claim 23, wherein the at least one biomarker is associated with a drug pathway of mechanism.

27. The method of claim 23, wherein the at least one biomarker is associated with deleterious toxicity.

28. The method of claim 23, wherein the at least one biomarker is associated with an immunomodulatory signal.

29. The method of claim 22, further comprising identifying at least one functional property associated with the subset of reagents.

30. The method of claim 22, wherein the first and the second clusters are identified based on distances between vectors associated with each pharmaceutical compound in the first cluster and distances between vectors associated with each pharmaceutical compound in the second cluster.

31. The method of claim 22, further comprising applying the k-means clustering algorithm to the plurality of normalized vectors.

32. The method of claim 22, wherein each reagent in the plurality of reagents is a mammalian cell line.

33. The method of claim 32, wherein each mammalian cell line is a cancer cell line.

34. The method of claim 22, wherein each reagent in the plurality of reagents is a protein.

35. The method of claim 34, wherein each protein in the plurality of reagents is a cell receptor.

36. The method of claim 34, wherein each protein in the plurality of reagents is an enzyme.

37. The method of claim 36, wherein each enzyme in the plurality of reagents is a kinase.

38. The method of claim 22, wherein at least one functional interaction is half-maximal inhibitory concentration ($IC_{50}$).

39. The method of claim 22, wherein at least one functional interaction is half-maximal effective concentration ($EC_{50}$).

40. The method of claim 22, wherein at least one functional interaction is area under the curve (AUC).

41. The method of claim 22, wherein a first component of a first vector in the plurality of vectors is associated with a first functional interaction of a first compound with a reagent in the plurality of reagents, and a second component of the first vector is associated with a second functional interaction of the first compound with the reagent.

* * * * *